(12) United States Patent
Raymond et al.

(10) Patent No.: US 12,245,811 B2
(45) Date of Patent: Mar. 11, 2025

(54) METHODS AND SYSTEMS FOR THICKNESS MEASUREMENTS USING SPECTRALLY RESOLVED FULL GRADIENT TOPOGRAPHY

(71) Applicant: AMO Development, LLC, Irvine, CA (US)

(72) Inventors: Thomas D. Raymond, Edgewood, NM (US); Daniel R. Neal, Tijeras, NM (US); Richard J. Copland, Albuquerque, NM (US)

(73) Assignee: AMO Development, LLC, Irvine, CA (US)

( * ) Notice: Subject to any disclaimer, the term of this patent is extended or adjusted under 35 U.S.C. 154(b) by 868 days.

(21) Appl. No.: 17/232,064

(22) Filed: Apr. 15, 2021

(65) Prior Publication Data

US 2022/0330813 A1      Oct. 20, 2022

(51) Int. Cl.
*A61B 3/10*    (2006.01)
*A61B 3/02*    (2006.01)
*A61B 3/12*    (2006.01)
*A61B 3/14*    (2006.01)

(52) U.S. Cl.
CPC ............... *A61B 3/101* (2013.01); *A61B 3/14* (2013.01)

(58) Field of Classification Search
CPC  A61B 3/113; A61B 3/02; A61B 3/102; A61B 3/1025; A61B 3/1015; A61B 3/103; A61B 3/1225; A61B 3/024; A61B 3/005
USPC ................ 351/209, 200, 205, 206, 210, 211, 351/221–223, 245–246
See application file for complete search history.

(56) References Cited

U.S. PATENT DOCUMENTS

| | | | |
|---|---|---|---|
| 5,317,389 A | 5/1994 | Hochberg et al. | |
| 5,777,719 A | 7/1998 | Williams et al. | |
| 6,550,917 B1 | 4/2003 | Neal et al. | |
| 7,980,699 B2 | 7/2011 | Neal et al. | |
| 8,437,008 B2 | 5/2013 | Fercher et al. | |
| 9,046,422 B2 | 6/2015 | Kudenov | |
| 9,913,579 B2 | 3/2018 | Frisken et al. | |
| 10,004,396 B2 | 6/2018 | Korb et al. | |
| 10,893,796 B2 | 1/2021 | Wang et al. | |
| 2018/0177391 A1 | 6/2018 | Korb et al. | |
| 2019/0117109 A1* | 4/2019 | Grundfest | A61B 5/4875 |

(Continued)

FOREIGN PATENT DOCUMENTS

WO      2019232575 A1      12/2019

OTHER PUBLICATIONS

Mejia-Barbosa Y., et al., "Object Surface For Applying A Modified Hartmann Test To Measure Corneal Topography," Applied Optics, Nov. 1, 2001, vol. 40 (31), pp. 5778-5786.

*Primary Examiner* — Dawayne Pinkney

(57) ABSTRACT

An apparatus and method: project a plurality of light spots onto a cornea of an eye having a tear film disposed thereon, wherein the light spots are broadband light spots or are narrowband light spots whose bandwidth is tuned in time across a broad bandwidth; image the light spots from the cornea onto at least one two-dimensional detector array; spectrally resolve each of the plurality of imaged light spots; perform interferometry on the spectrally resolved imaged light spots to identify an anterior interface and a posterior interface of the tear film of the eye; and determine a thickness of the tear film as a distance between the anterior interface and the posterior interface.

20 Claims, 16 Drawing Sheets

(56) References Cited

U.S. PATENT DOCUMENTS

2019/0183333 A1\* 6/2019 Arieli .................. A61B 3/1005
2019/0223714 A1\* 7/2019 Raymond .......... G01B 9/02004

\* cited by examiner

METHODS AND SYSTEMS FOR THICKNESS MEASUREMENTS USING SPECTRALLY RESOLVED FULL GRADIENT TOPOGRAPHY

TECHNICAL FIELD

Embodiments of this invention pertain to eye measurement systems and methods, and more particularly, to eye measurement systems and methods which can determine a thickness of an eye structure, in particular for example a thickness of a tear film, using spectrally resolves full gradient topography.

BACKGROUND

Various types of eye measurement instruments and methods are known, including autorefractors, wavefront aberrometers, corneal topographers and optical coherence topography (OCT) systems.

An autorefractor is a computer-controlled machine used during an eye examination to provide an objective measurement of the refractive error for an eye which can be used to generate a prescription for glasses or contact lenses. This is achieved by measuring how light is changed as it enters a person's eye.

Wavefront aberrometry measures the way a wavefront of light passes through the cornea and the crystalline lens of an eye, which are the refractive components of the eye. Distortions that occur as light travels through the eye are called aberrations, representing specific vision errors. Various types of wavefront aberrometers and methods are known, including Tscherning aberrometers, retinal ray tracing, and Shack-Hartmann aberrometers.

Corneal topography, also sometimes referred to as photokeratoscopy and videokeratoscopy, is a technique that is used to map the curved surface of the cornea. Corneal topography data can help measure the quality of vision as well as assist in eye surgery and the fitting of contact lenses. Various types of corneal topographers and methods are known, including Placido ring topographers, Scheimpflug imagers, and more recently, point source color LED topographers (CLT).

Optical coherence tomography (OCT) is a method of interferometry that determines the scattering profile of a sample along the OCT beam. OCT systems can operate in the time domain (TD-OCT) or the frequency domain (FD-OCT). FD-OCT techniques have significant advantages in speed and signal-to-noise ratio as compared to TD-OCT. The spectral information discrimination in FD-OCT is typically accomplished by using a dispersive spectrometer in the detection arm in the case of spectral domain OCT (SD-OCT) or rapidly scanning a swept laser source in the case of swept-source OCT (SS-OCT).

FIG. 1 is a schematic drawing of a portion of a human eye 101 which can be used in the explanations below. Eye 101 includes, in relevant part, a cornea 402, an iris 404, a lens 406, a sclera 408 and a retina 409.

Dry eye syndrome affects many people, but the quantification of this condition has been problematic both from a metric standpoint and from a measurement standpoint. Traditional metrics such as Tear Film Breakup Time (TFBUT), while easy to measure, are not repeatable and don't correlate to patient complaints about comfort or visual acuity degradation caused by tear film breakup.

Optical coherence tomography can at least in theory be used to measure the thickness of a tear film, but the axial resolution of these devices is marginal for the task, requiring ultrawide light sources, and scanning optics. For these reasons, the cost of OCT based tear film thickness measurement solution has been prohibitive.

Thus it is desired to provide a less expensive measurement instrument and method which can measure the tear film thickness in an eye.

SUMMARY OF THE INVENTION

In one aspect, a method comprises projecting a plurality of light spots onto an eye having a cornea and a tear film disposed thereon, wherein the light spots are broadband light spots or are narrowband light spots whose bandwidth is tuned in time across a broad bandwidth; imaging the light spots from the eye onto at least one two-dimensional detector array; spectrally resolving each of the plurality of imaged light spots; performing interferometry on the spectrally resolved imaged light spots to identify an anterior interface and a posterior interface of the tear film of the eye; and determining a thickness of the tear film as a distance between the anterior interface and the posterior interface.

In some embodiments, the light spots are broadband light spots, and wherein spectrally resolving each of the plurality of imaged light spots comprises projecting the imaged light spots onto the at least one two-dimensional detector array via a spectrally dispersive element.

In some embodiments, the spectrally dispersive element is a prism.

In some embodiments, the spectrally dispersive element is a grating.

In some embodiments, the spectrally dispersive element comprises at least one interference filter.

In some embodiments, the light spots are narrowband light spots whose bandwidth is tuned in time across a broad bandwidth, and projecting the light spots comprises: producing light for the light spots with at least one broadband light source; passing the light from at least one broadband light source through at least one frequency tunable filter to produce the narrowband light spots; and tuning the frequency tunable filter across the broad bandwidth over a time interval. A readout of image data from the at least one two-dimensional array is synchronized to the tuning of the frequency tunable filter to spectrally resolve each of the plurality of imaged light spots.

In some embodiments, performing interferometry on the spectrally resolved light spots comprises determining an oscillation period of a spectrum of the spectrally resolved light spots.

In another aspect, an apparatus comprises: a plurality of light sources configured to project a plurality of broadband light spots onto an eye having a cornea and a tear film disposed thereon; a two-dimensional detector array; an optical system adapted to image the light spots from the eye onto the two-dimensional detector array, wherein the optical system includes a spectrally dispersive element, wherein the spectrally dispersive element projects the imaged light spots onto the at least one two-dimensional detector array; and a processor. The processor is configured to: receive image data from the two-dimensional detector array, spectrally resolve each of the plurality of imaged light spots based on the received image data from the detector array, perform interferometry on the spectrally resolved imaged light spots to identify an anterior interface and a posterior interface of the tear film of the eye, and determine a thickness of the tear film as a distance between the anterior interface and the posterior interface.

In some embodiments, the spectrally dispersive element is a prism.

In some embodiments, the spectrally dispersive element is a grating.

In some embodiments, the spectrally dispersive element comprises at least one interference filter.

In some embodiments, the apparatus further comprises a second two-dimensional detector array, wherein the optical system is adapted to image the light spots from the cornea onto the second two-dimensional detector array, and wherein the processor is configured to determine a corneal topography from an output of the second two-dimensional detector array.

In some embodiments, the plurality of light sources comprises: a group of first light sources arranged around a central axis of the optical system, the group being separated from the axis by a radial distance defining an aperture in the group; and a Helmholz light source for projecting some of the light spots onto the cornea through the aperture, wherein the optical system includes an optical element having a focal length, f, and wherein the Helmholz light source is disposed to be in an optical path approximately one focal length, f, away from the optical element.

In some embodiments, the apparatus further comprises a structure having a principal surface with an opening therein around the central axis, wherein the group of first light sources is provided on the principal surface.

In some embodiments, the first light sources are arranged on the structure such that when the cornea has a predetermined shape, the images of the first light sources are uniformly spaced on a grid on the two-dimensional detector array.

In some embodiments, the processor is configured to perform interferometry on the spectrally resolved light spots by determining an oscillation period of a spectrum of the spectrally resolved light spots.

In yet another aspect, an apparatus comprises: at least one broadband light source configured to produce broadband light; a frequency tunable filter configured to receive the broadband light, wherein the frequency tunable filter is configured to output narrowband light, and wherein the frequency tunable filter is further configured to be tuned across a broad bandwidth over a time interval; a light projection arrangement configured to receive the narrowband light from the frequency tunable filter and to project a plurality of narrowband light spots onto an eye having a cornea and a tear film disposed thereon; a two-dimensional detector array; an optical system adapted to image the light spots from the cornea onto the two-dimensional detector array; and a processor. The processor is configured to: receive image data from the two-dimensional detector array, synchronized with the tuning of the frequency tunable filter across the broad bandwidth to spectrally resolve each of the plurality of imaged light spots, perform interferometry on the spectrally resolved imaged light spots to identify an anterior interface and a posterior interface of the tear film of the eye, and determine a thickness of the tear film as a distance between the anterior interface and the posterior interface.

In some embodiments, the light projection arrangement comprises: a group of first light emitters arranged around a central axis of the optical system, the group being separated from the axis by a radial distance defining an aperture in the group; and a Helmholz light source for projecting some of the light spots onto the cornea through the aperture, wherein the optical system includes an optical element having a focal length, f, and wherein the Helmholz light source is disposed to be in an optical path approximately one focal length, f, away from the optical element.

In some embodiments, the apparatus further comprises a structure having a principal surface with an opening therein around the central axis, wherein the group of first light emitters is provided on the principal surface.

In some embodiments, the first light emitters are arranged on the structure such that when the cornea has a predetermined shape, the images of the first light sources are uniformly spaced on a grid on the two-dimensional detector array.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

DETAILED DESCRIPTION

Exemplary embodiments of optical measurement systems and methods for measuring aberrations of an eye to illustrate various aspects and advantages of these devices and methods are described below. However, it should be understood that the principles involved in these devices and methods can be employed in a variety of other contexts, and therefore the novel devices and method disclosed and claimed here should not be construed as being limited to the example embodiments described below.

As used herein the term "light source" means a source of electromagnetic radiation, particularly a source in or near the visible band of the electromagnetic spectrum, for example, in the infrared, near infrared, or ultraviolet bands of the electromagnetic radiation. As used herein, the term "light" may be extended to mean electromagnetic radiation in or near the visible band of the electromagnetic spectrum, for example, in the infrared, near infrared, or ultraviolet bands of the electromagnetic radiation. As used herein, "approximately" means with 30% (i.e., +1-30%) of a nominal value.

As used herein, "broadband" light, "broadband light spots" and "broad bandwidth" refer to light whose energy occupies (i.e., full width at half maximum (FWHM)) a frequency band whose bandwidth is at least 40% of the center frequency. In some embodiments, the FWHM bandwidth may be greater than 50% of the center frequency. In some embodiments, such broadband light may occupy at least the majority of the visible spectrum from 400 nm to 790 nm (in frequency, a broadband bandwidth from about 380 to 750 Terahertz (THz)). In some embodiments, the broadband light may substantially occupy (FWHM) the wavelengths from 420 nm to 730 nm (in frequency, a broadband bandwidth from about 410 to 714 Terahertz (THz)).

As used herein, "narrowband light," "narrowband light spots," and "narrow bandwidth" refer to light which whose energy occupies (i.e., full width at half maximum (FWHM)) a frequency band whose bandwidth is less than 20% of the center frequency. In some embodiments, the FWHM bandwidth may be less than 10% of the center frequency. In some embodiments, the narrowband light may substantially occupy (e.g., full width at half maximum (FWHM)) wavelengths spanning less than 40 nm at a wavelength of 550 nm (in frequency, a narrow bandwidth of about 37 THz at a center frequency of about 545 THz); in other embodiments less than 25 nm at a wavelength of 550 nm (in frequency, a narrow bandwidth of about 23 THz); and in still other embodiments less than 13 nm at a wavelength of 550 nm (in frequency, a narrow bandwidth of about 13 THz). In general, the range of occupied wavelengths will be greater at high center wavelengths (e.g., 700 nm) than at lower center wavelengths (e.g., 450 nm).

Figure 1:
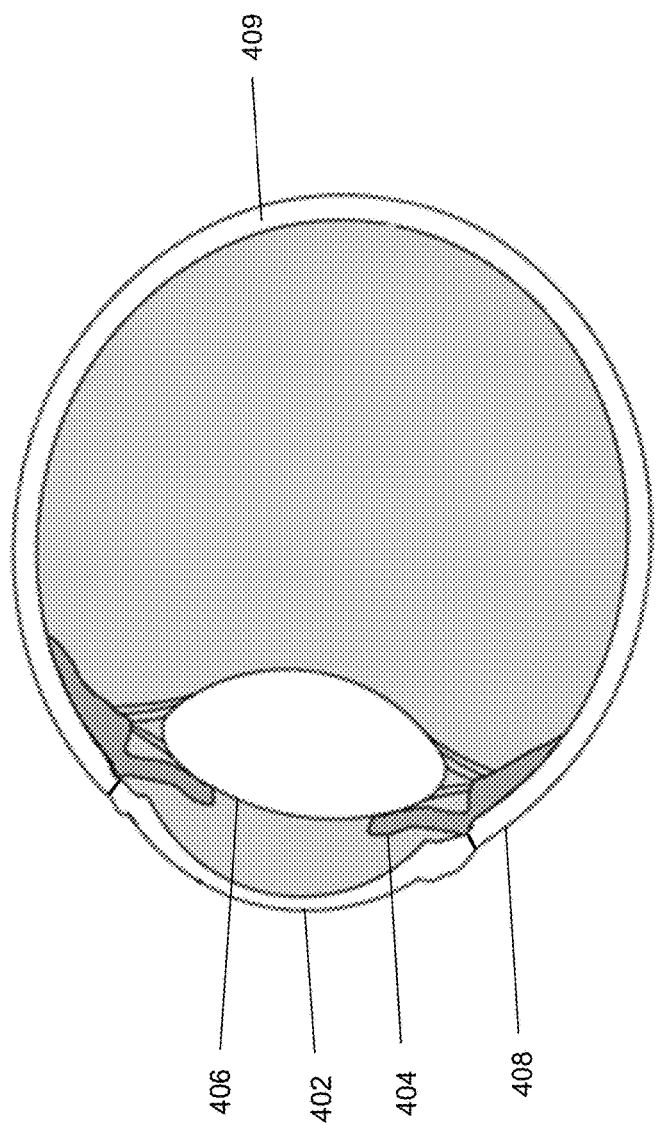
FIG. 1 is a schematic drawing of a portion of a human eye.
Figure 2:
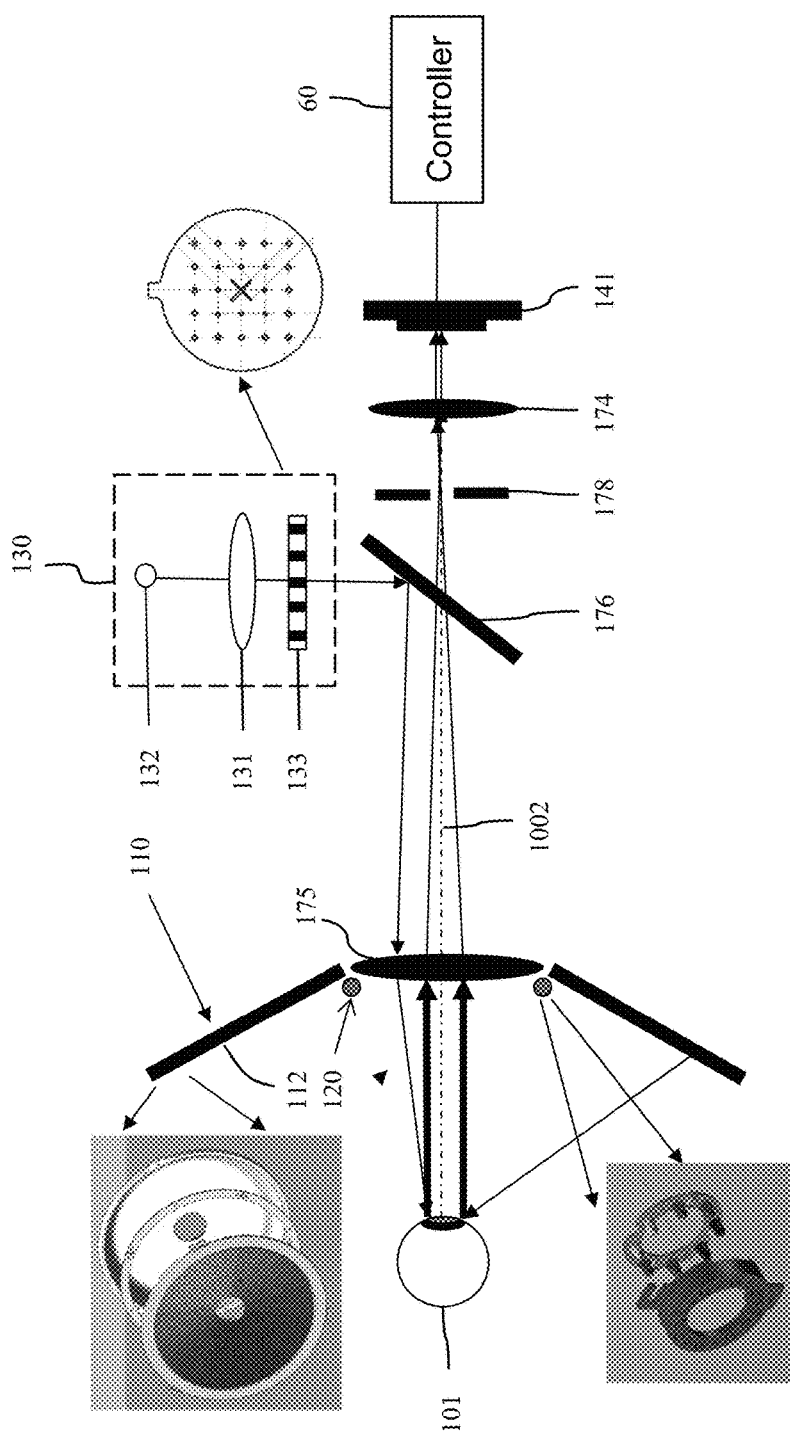
FIG. 2 illustrates an embodiment of a corneal topographer.

FIG. 2 illustrates an embodiment of a corneal topographer 2000.

Corneal topographer 2000 comprises a structure 110 having a principal surface with an opening or aperture 1140 therein; a plurality of first (or peripheral) light sources 120 provided on the principal surface 112 of the structure 110; a plurality of second, or central, light sources 130 (also sometimes referred to as "Helmholtz light sources"); a detector array 141; a controller 60, including a processor and memory; and an optical system disposed along a central axis 1002 passing through the opening or aperture of the structure 110. Optical system 1700 comprises a first lens 175, a beamsplitter 176, and a structure including an aperture 178, and a second lens 174.

In one embodiment, structure 110 has the shape of an elongated oval or "zeppelin" with openings or apertures at either end thereof. However, such a structure has ergonomic disadvantages and may be more difficult to construct than other structures. Accordingly, in some embodiments, principal surface 112 of structure 110 is concave when viewed from the cornea of eye 101.

In one embodiment where principal surface 112 is concave, principal surface 112 has the shape of a conical frustum. Alternatively, principal surface 112 may have a shape of hemisphere or some other portion of a sphere, with an opening or aperture therein. Also alternatively, principal surface 112 may have the shape of a modified sphere or conical frustum, with a side portion removed. Beneficially, such an arrangement may improve the ergonomics of corneal topographer 2000 by more easily allowing structure 1100 to be more closely located to a subject's eye 101 without being obstructed by the subject's nose. Of course, a variety of other configurations and shapes for principal surface 112 are possible.

In the embodiment of FIG. 2, the plurality of first light sources 120 are provided on the principal surface 112 of structure 110 so as to illuminate the cornea of eye 101. In one embodiment, light sources 120 may comprise individual light generating elements or lamps, such as light emitting diodes (LEDs) and/or the tips of the individual optical fibers of a fiber bundle. Alternatively, principal surface 112 of structure 110 may have a plurality of holes or apertures therein, and one or more backlight lamps, which may include reflectors and/or diffusers, may be provided for passing lighting through the holes to form the plurality of first light sources 120 which project light onto the cornea of eye 101. Other arrangements are possible.

In another embodiment, structure 110 is omitted from system 1000, and the first light sources 120 may be independently suspended (e.g., as separate optical fibers) to form a group of first light sources 120 arranged around central axis 1002, the group being separated from central axis 1002 by a radial distance defining an aperture in the group (corresponding generally to the aperture in the structure 110 illustrated in FIG. 2).

In one embodiment, second light sources 130 comprise a plurality of lamps, such as LEDs or optical fiber tips. Alternatively, second light sources 130 may comprise a plurality of holes or apertures in a surface that are illuminated by one or more backlight lamps with reflectors and/or diffusers, as shown in FIG. 2.

In one embodiment, second light sources 130 are located off the central optical axis 1002 of system 1000, and light from second light sources is directed toward optical lens 175 by beamsplitter 176.

Beneficially, each of the second light sources 130 is located approximately one focal length, f, away from optical element lens 175.

Two-dimensional detector array 141 comprises a plurality of light detecting elements arranged in a two dimensional array. In one embodiment, two-dimensional detector array 141 comprises such a charge-coupled device (CCD), such as may be found in a video camera. However, other arrangements such as a CMOS array, or another electronic photo-sensitive device, may be employed instead. Beneficially, the video output signal(s) of two-dimensional detector array 141 are provided to a processor if controller 60 which processes these output signals as described in greater detail below.

Lens 175 has an object side (e.g., towards eye 101) and an image side (e.g., towards two-dimensional detector 141). Lens 175 defines an object space located on the object side a finite distance from the lens, and an image space conjugate the object space. First light sources 120 are located an optically finite distance from the object space, and second light sources 130 are located at an optical infinity with respect to the object space. Lens 175 is configured to provide an image within the image space when a reflective surface, such as a cornea, is disposed within the object space. Lens 175 has a focal length, f, that is adapted to project collimated light from each of the second light sources 1300 through the opening or aperture of structure 110 (or through the aperture defined by the group of first light sources 120, when structure 1100 is omitted) onto the cornea of eye 101.

The arrangement of second light sources 130 insures that light from each of the second light sources 130 exiting lens 175 is collimated as it travels toward the corneal surface and makes an angle α to optical axis 1002 that is the arc tangent of the ratio of the focal length, f, of lens 175 and the radial distance of the particular light source 130 from optical axis 1002, i.e. the center of the aperture.

Corneal topographer 2000 employs second light sources 130 that may be configured according to the Helmholtz principle. In such embodiments, the second light sources 1300 are located at optical infinity with respect to eye 101. The Helmholtz principle includes the use of such infinite sources in combination with a telecentric detector system: i.e., a system that places the detector array at optical infinity with respect to the surface under measurement, in addition to insuring that the principal measured ray leaving the surface is parallel to the optical axis of the instrument. The Helmholtz corneal measurement principle has second light sources 130 at optical infinity and the telecentric observing system so that two-dimensional detector array 141 is also optically at an infinite distance from the images of the sources formed by the cornea. Naturally such a measurement system is insensitive to axial misalignment of the corneal surface with respect to the instrument.

Aperture (or stop) 178 influences the operation of corneal topographer 2000 in several ways.

First, the size of aperture 178 sets the solid angle of rays that can be accepted and passed to two-dimensional detector array 141. This solid angle in turn sets the area of the corneal surface that is sampled by any given light source spot. This may be understood by thinking of the image of a given light source to be located as a virtual image posterior to the corneal surface. Projecting forward from this spot image is a cone of rays; the solid angle that the detector can 'see'. The intersection of this cone with the cornea surface defines the area of that surface sampled by the light source spot. So setting the size of aperture 178 localizes the area of the cornea that a given light source samples.

Second, because the sampled area size is set by the size of aperture 178, it sets the amount of light that any single light source spot deposits on two-dimensional detector array 141. Thus if aperture 178 is made too small, the spots images are too dim.

Third, the size of aperture 178 sets the depth of focus of the detector system. If aperture 178 is too large and the virtual images created by the cornea lie in different planes due to the fact that the power of the cornea, i.e. its curvature, is different in different areas, it becomes hard to get all images in sharp enough focus on two-dimensional detector array 141 to achieve good image processing results. This can be a problem when measuring a case of keratoconus.

Figure 3:
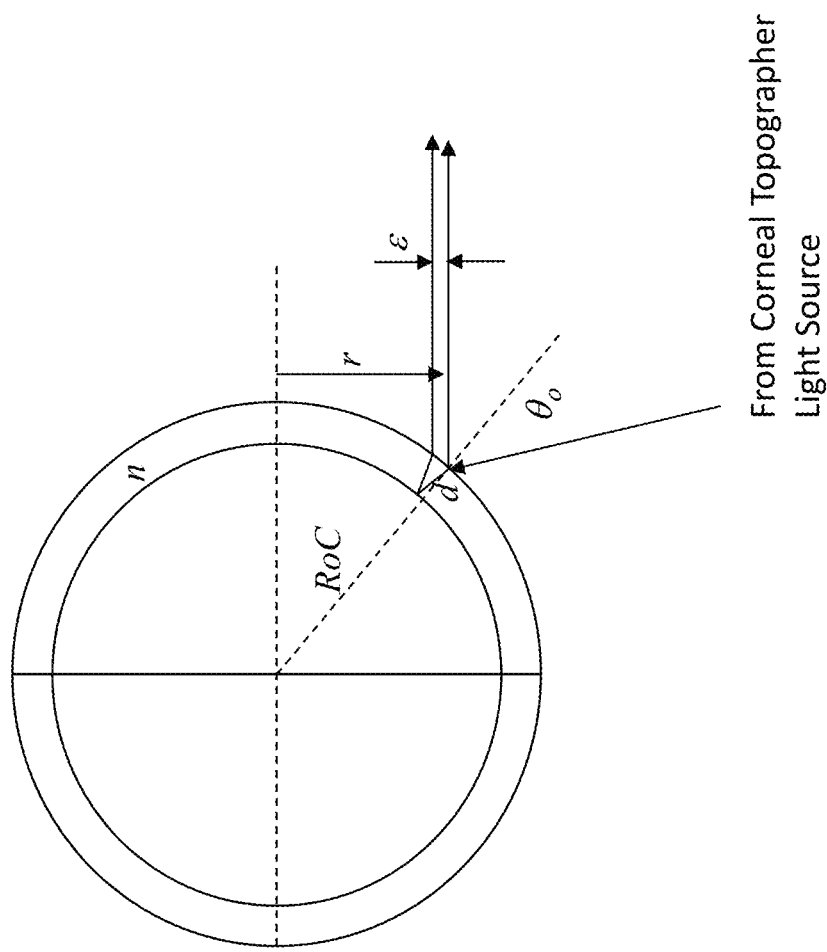
FIG. 3 is a diagram for explaining a first order calculation of rays from different surfaces of an eye.

FIG. 3 is a diagram for explaining a first order calculation of rays from different surfaces of an eye, for example an anterior and posterior surface of the cornea, or the anterior and posterior surface of a tear film which is disposed on a cornea. With respect to FIG. 3, it can be shown that:

$$\sin(\theta_o) = n\sin(\theta_i)$$

$$\varepsilon = 2d\sin(\theta_i)$$

$$r \cong RoC\sin(\theta_o)$$

$$\tau = 2d\sqrt{1 - \left(\frac{Sin(\theta_o)}{n}\right)}$$

and as a result:

$$\varepsilon \cong \frac{2dr}{nRoC}$$

where: n is the index of refraction of the material spanning the two surfaces (e.g., the index of refraction of the cornea, or of the tear film); RoC is the radius of curvature; r is the offset distance of the light beams from the optical axis; e is the distance between the two reflection beams from the two surfaces; and d is the distance between the two surfaces, which might define the thickness of the cornea, or the thickness of the tear film, for example.

Figure 4:
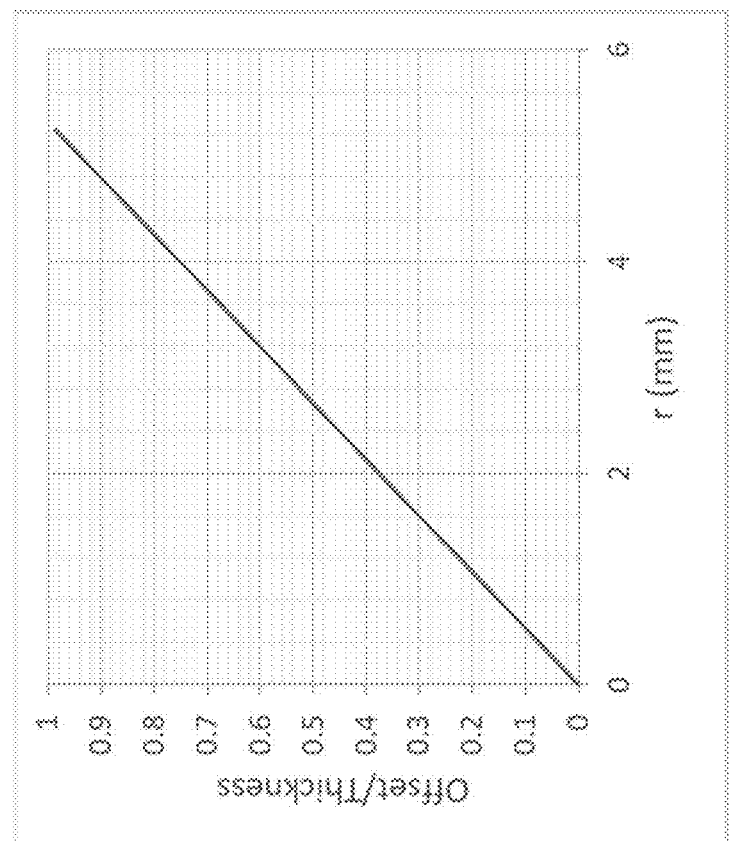
FIG. 4 illustrates an example relationship between a radial distance from an optical axis and the offset/thickness which is to be determined.

FIG. 4 illustrates an example relationship 4000 between a radial distance from an optical axis and the offset/thickness which is to be determined.

Figure 5:
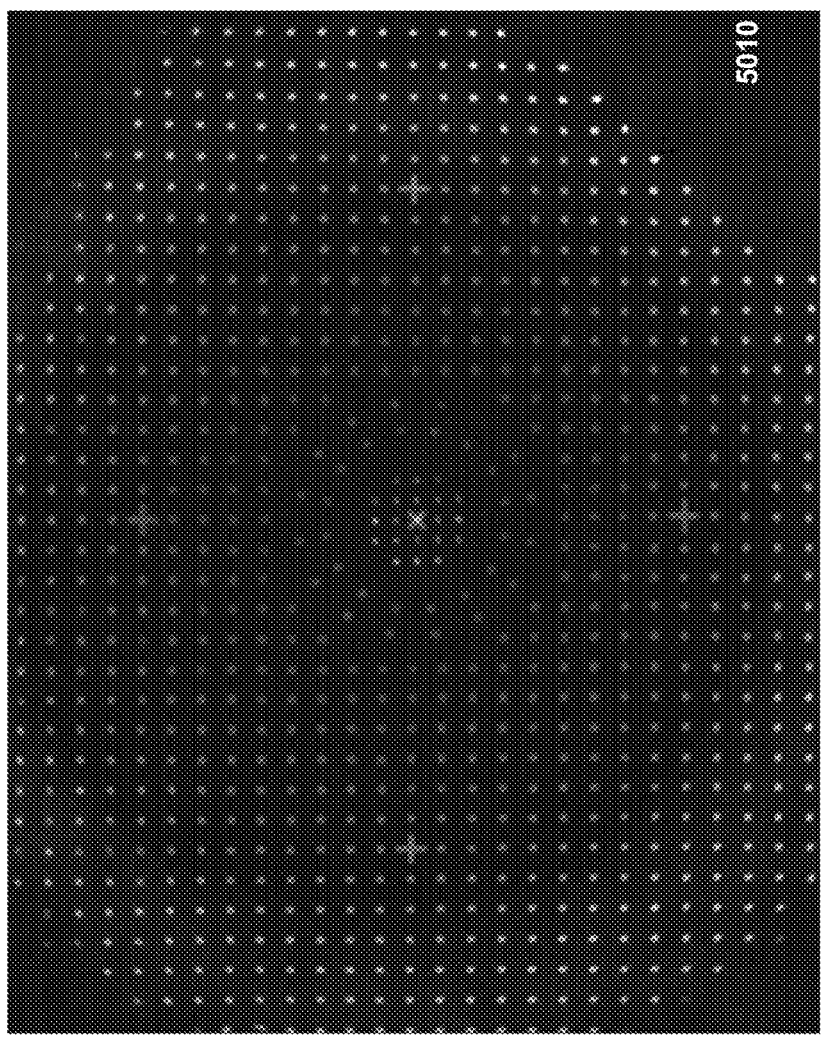
FIG. 5 illustrates a pattern of light spots produced on a two-dimensional detector array in the corneal topographer of FIG. 2.

FIG. 5 illustrates a pattern 5000 of light spots 5010 produced on a two-dimensional detector array in the corneal topographer of FIG. 2. Here, in some embodiments typical spot sizes may vary across the detector array but are on the order of 50 um in diameter. For good interference detection, the light spot offset should remain less than 20% of the spot diameter, i.e., d≤10 mm. For a tear film thickness of about 10 mm, the overlap will be good over 10 mm diameter coverage of the eye.

For colinear beams that are spatially overlapped, the interference is observed in the spectrum and is trigonometrically related to the round trip delay time between the reflecting beams:

$$S(\omega) = \sum_{j=0}^{N} I_j(\omega) + \sum_{j \neq l}^{N} \sqrt{I_j(\omega) * I_l(\omega)} \, Cos(\omega \tau_{jl})$$

$$\tau_{jl} = 2d_{jl}\sqrt{1 - \left(\frac{Sin(\theta_o)}{n_{jl}}\right)}$$

Figure 6:
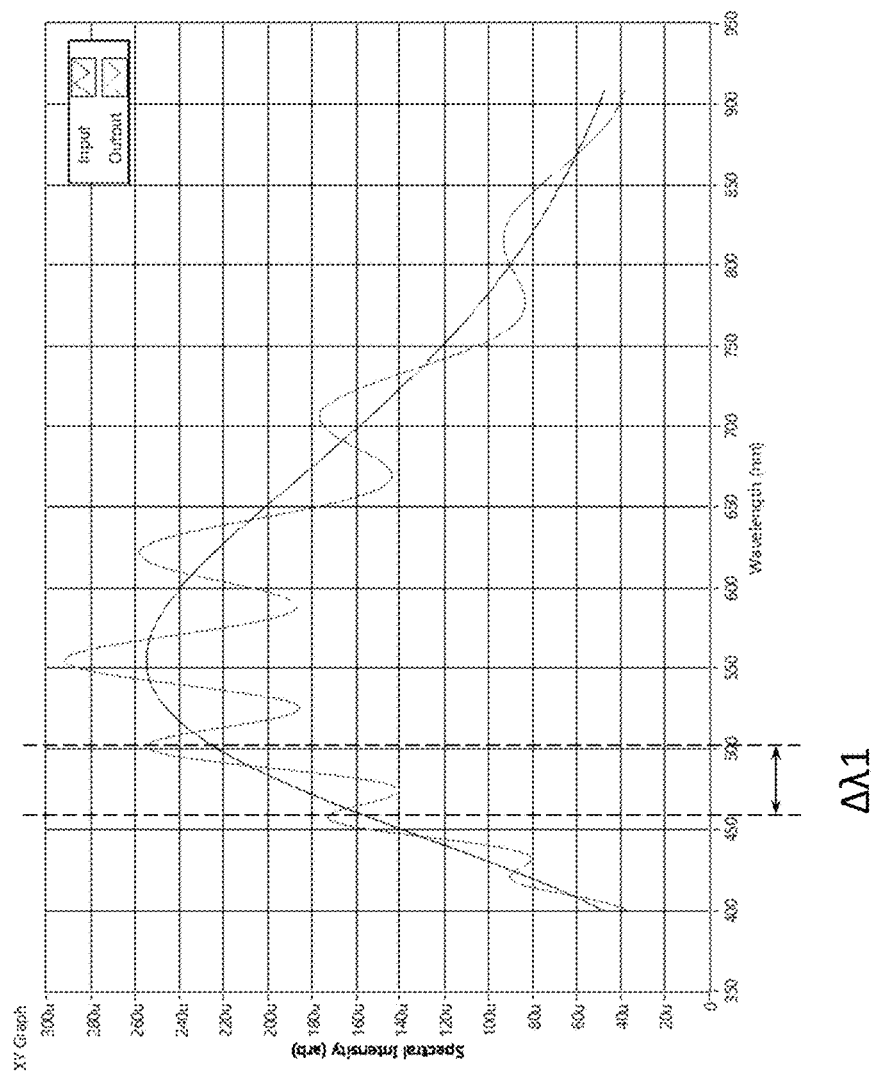
FIG. 6 illustrates a first example of a spectral intensity plot of reflected light from a tear film and cornea of an eye for a first tear film thickness.

FIG. 6 illustrates a first example of a spectral intensity plot 6000 of reflected light from a tear film and cornea of an eye for a first tear film thickness. Here the optical two-pass tear optical thickness is 5 um and the lipid layer two-pass optical thickness is 250 nm.

The lipid-aqueous tear reflection is modeled as 0.1% of the air-lipid interface reflection, and the eye-aqueous reflection is 1% of the same. The dark curve is the input beam spectrum, and the lighter curve with the oscillations, demonstrating the interference effect, is the spectrum of the combined reflected beams. Here, the wavelength period of the oscillation, $\Delta\lambda 1$, in the vicinity of 450 nm is about 43 nm.

Figure 7:
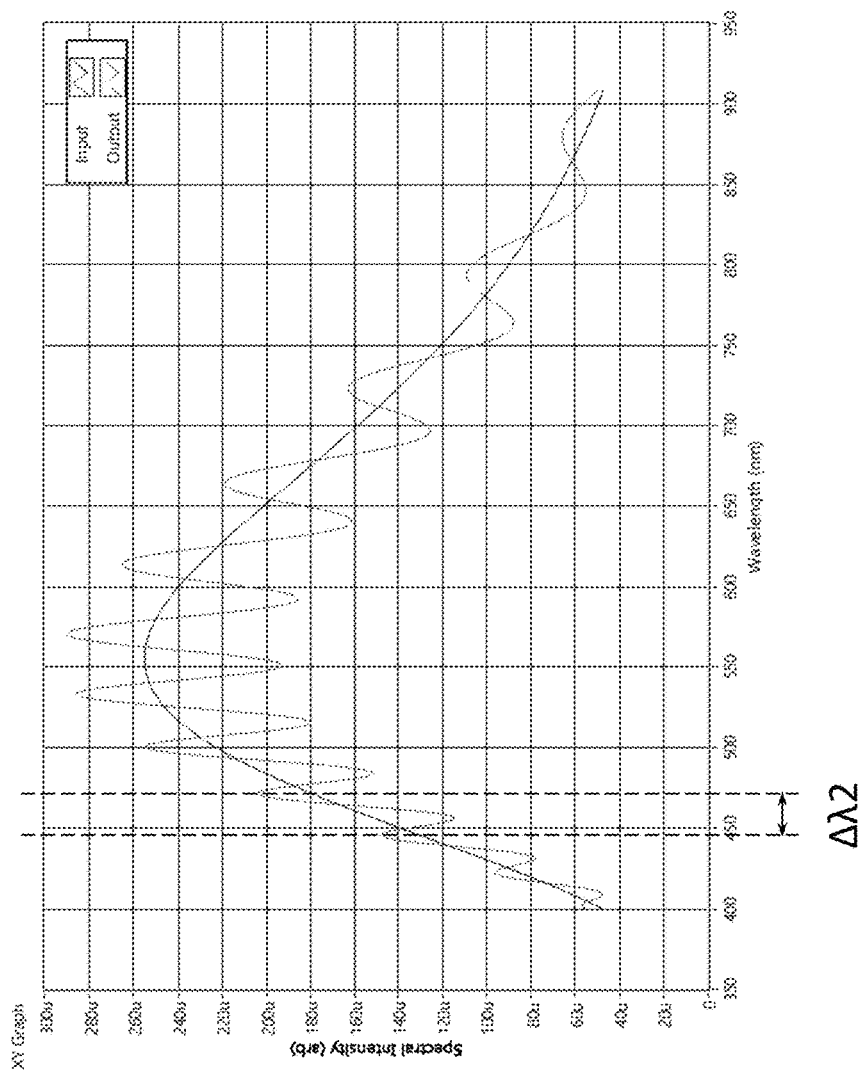
FIG. 7 illustrates a second example of a spectral intensity plot of reflected light from a tear film and cornea of an eye for a second tear film thickness.

FIG. 7 illustrates a second example of a spectral intensity plot 7000 of reflected light from a tear film and cornea of an eye for a second tear film thickness. Here the optical two-pass tear optical thickness is 8 um and the lipid layer two-pass optical thickness is 250 nm.

Again, the lipid-aqueous tear reflection is modeled as 0.1% of the air-lipid interface reflection, and the eye-aqueous reflection is 1% of the same. As before, the dark curve is the input beam spectrum, and the lighter curve with the oscillations, demonstrating the interference effect, is the spectrum of the combined reflected beams. Here, the wavelength period of the oscillation, $\Delta\lambda 2$, in the vicinity of 450 nm is about 25 nm.

From FIGS. 6 and 7, we observe that the period of the oscillation diminishes when the aqueous layer thickness is increased. Clearly an imaging spectrometer with modest spectral resolution will suffice for determining the thickness. Alternately a tunable narrowband light source can be used with a conventional imager set up to capture multiple images. This approach can have high transverse resolution, at the expense of slower frame rate. Beneficially, motion of the eye will not, to a first order, affect the fringe frequency.

From all of this, an arrangement emerges for measuring the tear film of the eye using a variation of corneal topographer 2000.

Here, a full gradient topographer similar to corneal topographer 2000 is employed wherein a cone is placed in front of the patient's, or subject's, eye 101 with a back illuminated mask with many (e.g., 1000) holes, each of which acts as a point source of light for projecting a corresponding light spot onto an eye 101, whereby the light passes through the tear film. The back illumination may be produced via LEDs that may operate in the near infrared wavelengths. The light from each point source reflects off the tear film—air interface and into collection optics.

Beneficially, the collection optics are configured in telecentric imaging mode to collect reflected light that travels parallel to the optical axis of the collection optics. The reflected light is imaged with a two-dimensional sensor to yield an array of spots whose locations can be related to the local gradient of the reflection surface. While the full-gradient topographer could in principle measure other surfaces present on the cornea, in practice the spots from those surfaces are not easily spatially resolved from the main reflection because the lateral displacements are small and the reflections from these other surfaces is about 100 times weaker than the primary reflection. In the full gradient corneal topographer, the imaging may be done without regard to spectral content, but in fact, the spectral content of each point image may be modified by reflections from underlying surfaces such as the lipid layer, the tear film layer, and even the posterior surface of the cornea, provided the reflections overlap the primary reflection at the tear film-air interface. Because the spectral influence is an interferometric effect, even weak reflections can have a significant influence because it is the ratio of electric field amplitudes that drives the spectral fringe depth. By spectrally resolving each spot and analyzing using well-known methods (e.g., SD OCT), this information may be discerned.

A method of spatially resolved spectrometry may be similar to hyperspectral imaging often used in remote sensing from aerial devices such as drones and satellites. It may also be similar to like spectral domain OCT, but in this case, multiple beams are simultaneously incident on the cornea. As with spectral domain OCT, the breadth of the light source will determine the axial resolution while the resolving power of the spectrometer determines the thickest film that can be measured. Unlike OCT, the light need not be derived from a single light source, but can rather be provided by several discrete LEDs in the back illumination that could be simultaneously turned on.

The spectral resolving power and bandwidth which are required depend on the film thickness to be measured since this determines the fringe period on the spectrum. Thin films such as lipid layers (50 nm) have fringe spacings that are well over 150 nm in the visible and may produce one, or a fraction of an oscillation, in the visible spectrum. Thicker films, such as the aqueous of the tear film (5-8 um), produce fringes with spectral spacing around 50-75 nm which are easily resolved with a modest spectrally dispersive element, but which are invisible to a color camera. Finally, with increased spectral resolution, this technique is extendable to measurement of the corneal thickness (750 um); in combination with the normal full gradient topography analysis, the pachymetry will reveal the corneal toric power.

Figure 8:
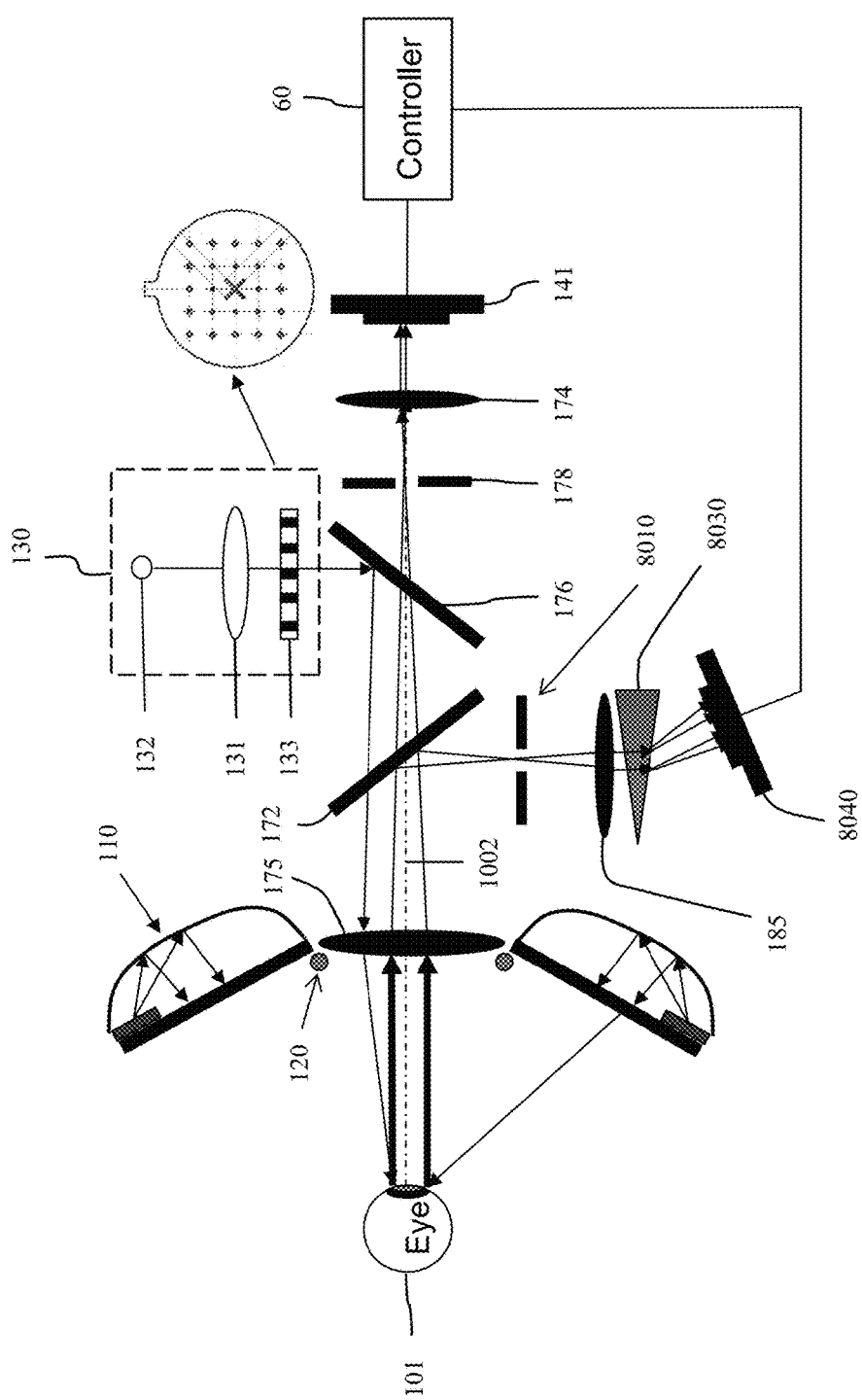
FIG. 8 illustrates a first embodiment of an apparatus which can measure tear film thickness.

FIG. 8 illustrates a first embodiment of an apparatus 8000 which can measure tear film thickness. Apparatus 8000 is similar to corneal topographer 2000 and a description of like elements will not be repeated for brevity.

In lieu of a plurality of individual light elements, apparatus 8000 employs a cone 110 placed in front of the patient's, or subject's, eye 101, with a back illuminated mask with many (e.g., $\approx 1000$) holes, each of which acts as a point source of light and projects a corresponding light spot onto eye 101, including the cornea and the tear film disposed thereon.

Apparatus 8000 also includes in it optical path a second aperture 8010, a lens 185, a spectrally dispersive element 8030 and a second two-dimensional detector array 8040 for receiving imaged light spots from 101 via spectrally dispersive element 8030. Spectrally dispersive element 8030 is a prism, but in other embodiments it may be a grating, or an interference filter. The combination of spectrally dispersive element 8030 and second two-dimensional detector array 8040 spectrally resolves the imaged light spots from eye 101. The processor in controller 60 performs interferometry on the spectrally resolved imaged light spots to identify an anterior interface and a posterior interface of the tear film of eye 101, as discussed above; and determines the thickness of the tear film as a distance between the anterior interface and the posterior interface.

Figure 9:
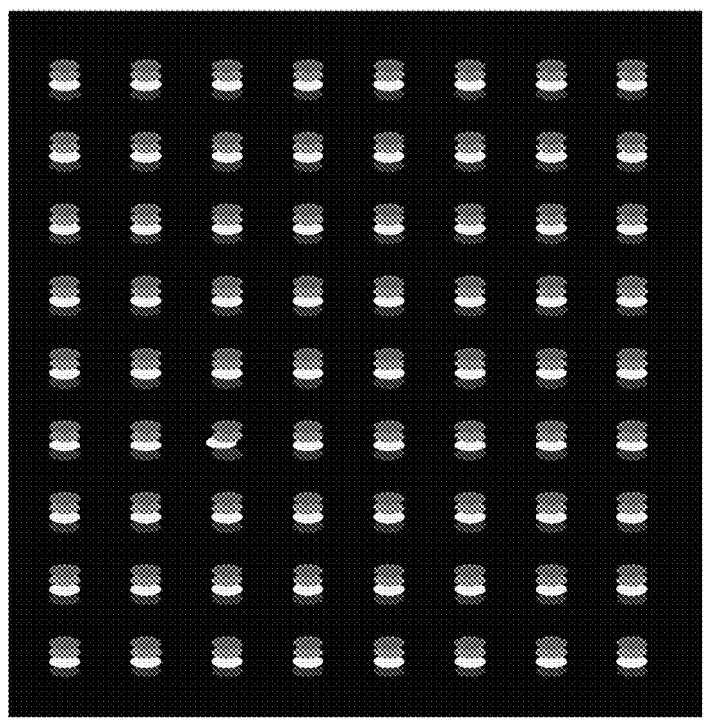
FIG. 9 illustrates an example of an array of light sources which may be included in the apparatus of FIG. 8.

FIG. 9 illustrates an example of an array 9000 of light sources which may be included in the apparatus of FIG. 8. As shown in FIG. 9, broadband back illumination could be provided by a bank of discrete LEDs—e.g., lighting elements each comprising a red, a blue and a green LED.

Figure 10:
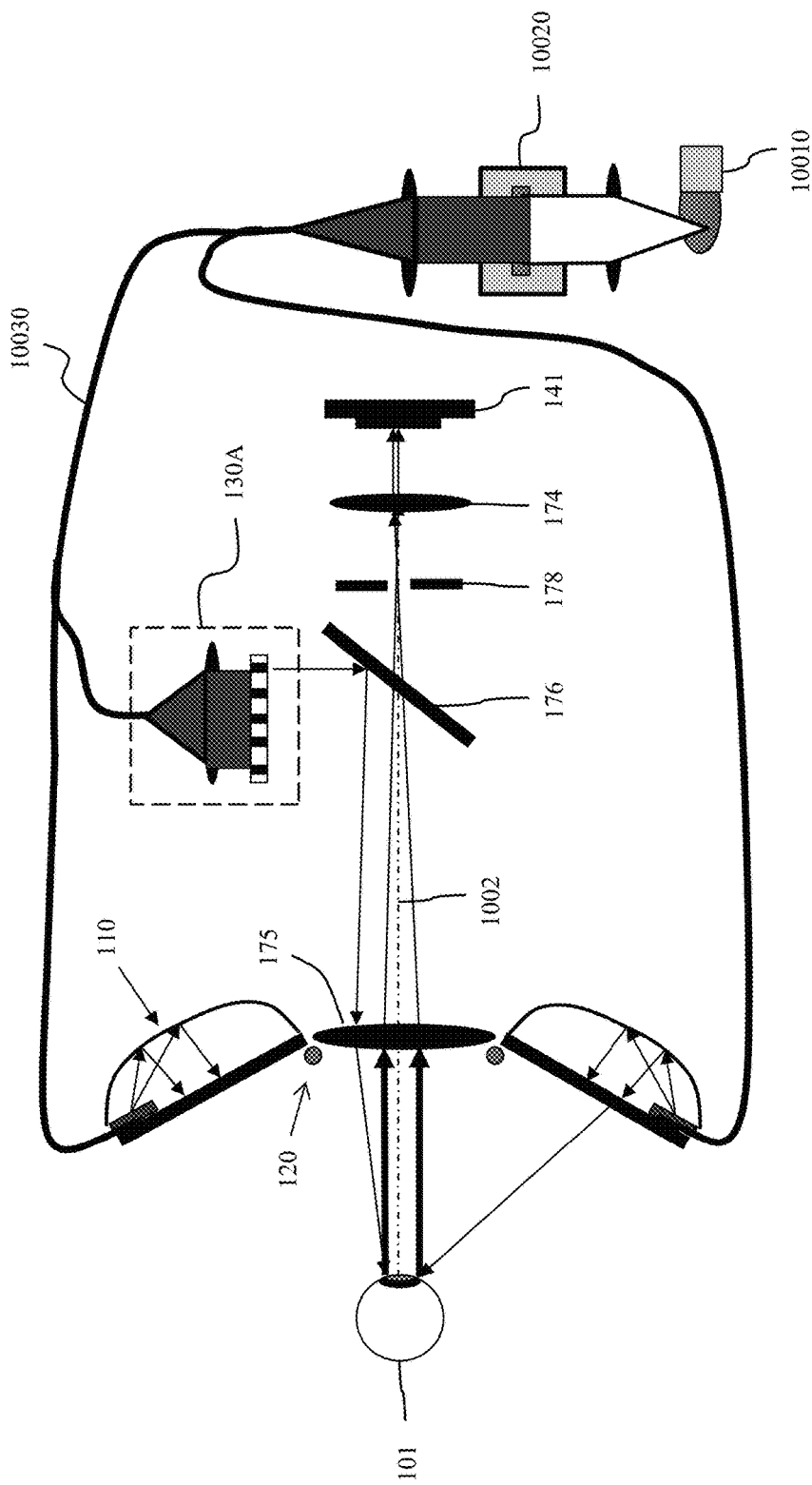
FIG. 10 illustrates a second embodiment of an apparatus which can measure tear film thickness.

FIG. 10 illustrates a second embodiment of an apparatus 10000 which can measure tear film thickness. Apparatus 10000 is similar to corneal topographer 2000 and a description of like elements will not be repeated for brevity. In comparison to apparatus 8000, rather than employing a spectrally dispersive element to spectrally resolve the imaged light spots from eye 101, apparatus 10000 employs a spectrally tunable, or spectrally swept, light source. Here this is achieved with a single broadband light source 10010 that is swept or scanned in time (like swept source OCT) with a frequency tunable filter 10020 and whose output projects the light spots on eye by a light projection arrangement comprising light distribution element 10030 and the light sources for the corneal topographer of elements 110 and 130 (Helmholz source). One example of such a frequency tunable filter is produced by Meadowlarks optics as model TOF-SV. The combination produces narrowband light spots at any given time which are swept in time across a broad bandwidth. For example, in some embodiments the narrowband light spots FWHM bandwidth may be less than 10% of the center frequency. In some embodiments, the narrowband light may substantially occupy (e.g., full width at half maximum (FWHM)) wavelengths spanning less than 40 nm at a wavelength of 550 nm (in frequency, a narrow bandwidth of about 37 THz at a center frequency of about 545 THz); in other embodiments less than 25 nm at a wavelength of 550 nm (in frequency, a narrow bandwidth of about 23 THz); and in still other embodiments less than 13 nm at a wavelength of 550 nm (in frequency, a narrow bandwidth of about 13 THz). In general, the range of occupied wavelengths will be greater at high center wavelengths (e.g., 700 nm) than at lower center wavelengths (e.g., 450 nm). In some embodiments, the narrowband light spots may be swept across a broadband bandwidth corresponding to wavelengths from about 420 nm to 730 nm.

The output of two-dimensional detector array 141 is synchronized in time with the sweep of the light to spectrally resolve the imaged light spots. As before, a processor in controller 60 performs interferometry on the spectrally resolved imaged light spots to identify an anterior interface and a posterior interface of the tear film of eye 101, as discussed above; and determines the thickness of the tear film as a distance between the anterior interface and the posterior interface.

In an alternative embodiment to apparatus 10000, the frequency sweep could be achieved by time sequence multiplexing a series of discrete LEDs having different colors or light output spectrums. Again, the output of two-dimensional detector array 141 is synchronized in time with the sweep of the light to spectrally resolve the imaged light spots. As before, a processor in controller 60 performs interferometry on the spectrally resolved imaged light spots to identify an anterior interface and a posterior interface of the tear film of eye 101, as discussed above; and determines the thickness of the tear film as a distance between the anterior interface and the posterior interface.

Figure 11A:
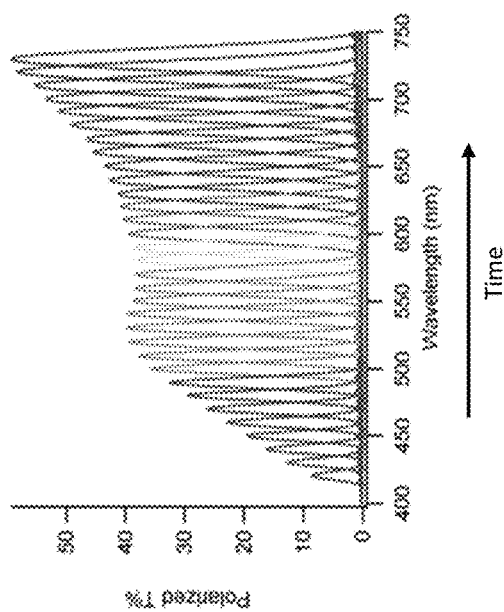
FIG. 11A illustrates an example of a frequency response of a tunable filter which is included in the apparatus of FIG. 10.

FIG. 11A illustrates an example of a frequency response 11000 of a tunable filter which is included in the apparatus of FIG. 10.

Figure 11B:
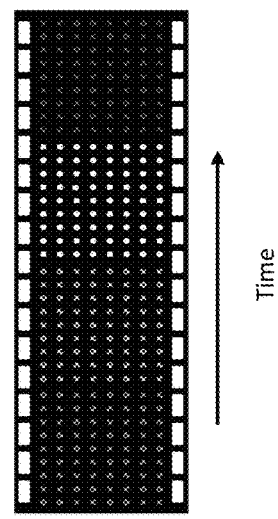
FIG. 11B shows a plot which illustrates how the spectral wavelengths/frequencies of light spots imaged onto a two-dimensional detector array vary with time as the passband of the tunable filter is swept in frequency across a broad bandwidth.

FIG. 11B shows a plot 11010 which illustrates how the spectral wavelengths/frequencies of light spots imaged onto a two-dimensional detector array vary with time as the passband of the tunable filter is swept in frequency across a broad bandwidth.

Figure 12:
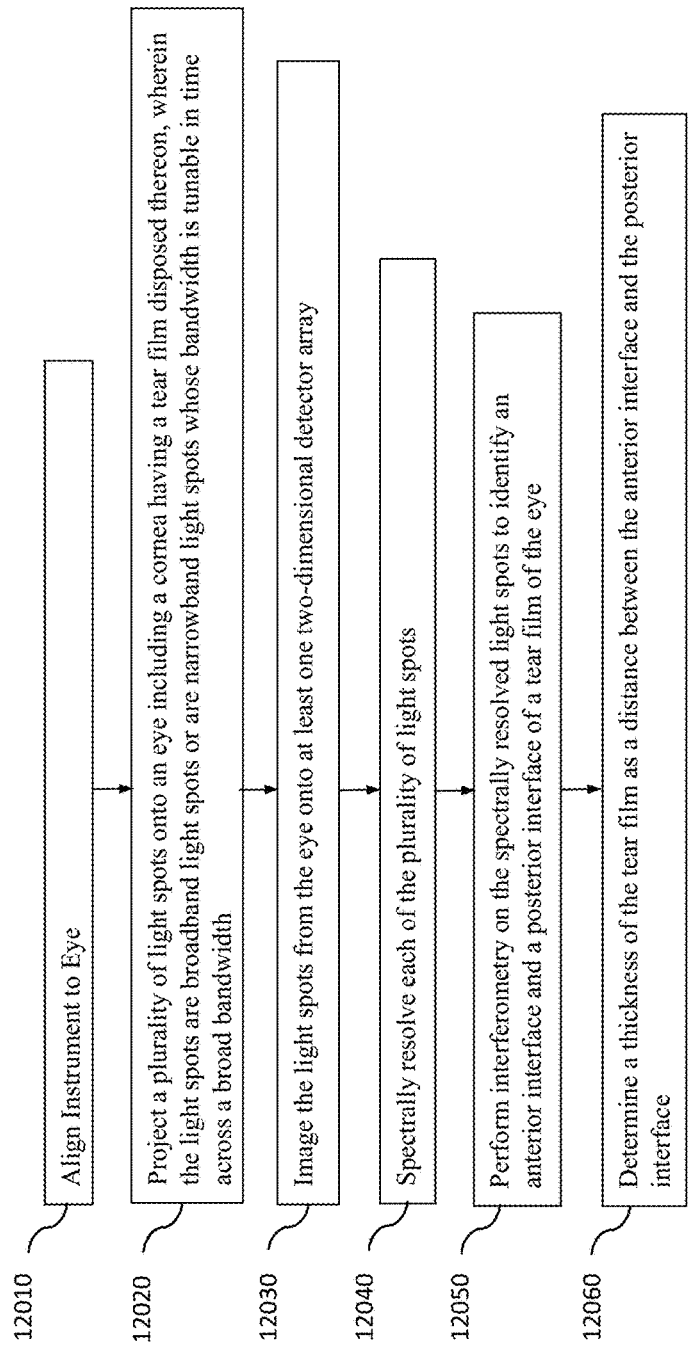
FIG. 12 is a flowchart of an example embodiment of a method of measuring an optical characteristic of an eye.

FIG. 12 is a flowchart of an example embodiment of a method 5000 of measuring one or more characteristics of an eye with an eye measurement instrument.

An operation 12010 includes aligning an eye measurement instrument to an eye.

An operation 12020 includes projecting a plurality of light spots onto an eye including a cornea having a tear film disposed thereon, wherein the light spots are broadband light spots or are narrowband light spots whose bandwidth is tunable in time across a broad bandwidth.

An operation 12030 imaging the light spots from the eye onto at least one two-dimensional detector array.

An operation 12040 includes spectrally resolving each of the plurality of light spots.

An operation 12050 includes performing interferometry on the spectrally resolved light spots to identify an anterior interface and a posterior interface of a tear film of the eye.

An operation 12060 includes determining a thickness of the tear film as a distance between the anterior interface and the posterior interface.

In some embodiments, some or all of the operations 12040, 12050 and 12060 may be performed by a properly-programmed processor, such as the processor in controller 60 as disclosed above with respect to FIGS. 8 and 10.

The principles of a split-prism rangefinder system as described above may be applied to an optical measurement instrument which includes additional functionality, such as the ability to measure corneal topography and/or to make wavefront aberrometry measurements for they eye. Embodiments of such an optical measurement instrument, and methods of operation thereof, will now be described.

Figure 13C:
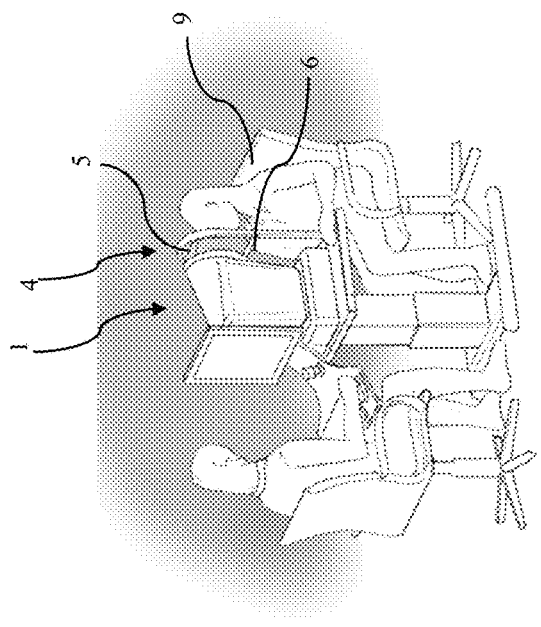
FIG. 13C illustrates a side perspective view showing an optical measurement system according to many embodiments.
Figure 13A:
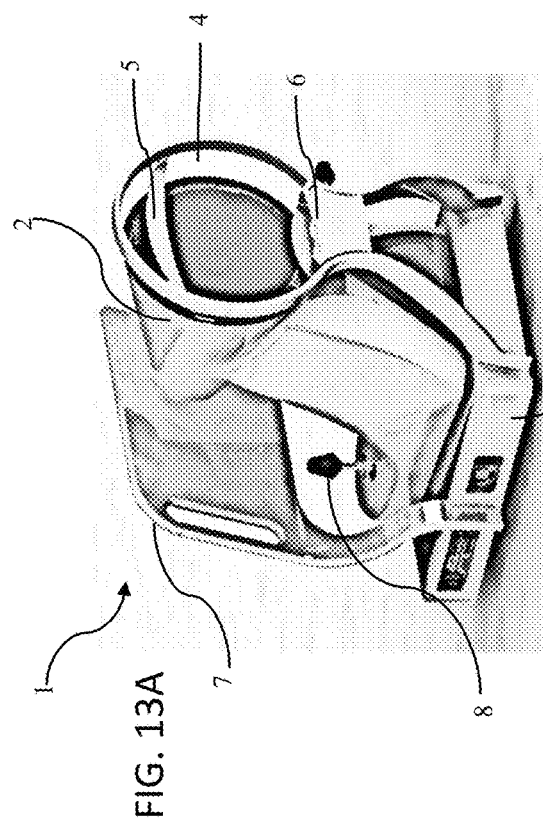
FIG. 13A illustrates a front perspective view showing an optical measurement system according to many embodiments.
Figure 13B:
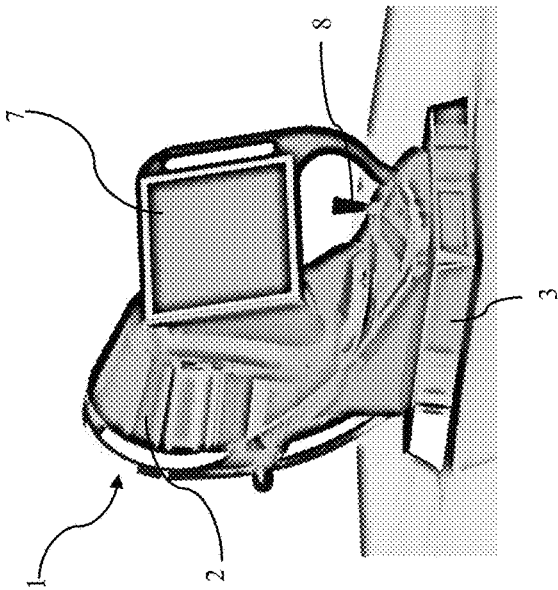
FIG. 13B illustrates a rear perspective view showing an optical measurement system according to many embodiments.

As shown in FIGS. 13A-13C, an optical measurement system 1, according to many embodiments, is operable to provide for a plurality of measurements of the human eye, including wavefront aberrometry measurements, corneal topography measurements, and optical coherence tomography measurements to measure characteristics of the cornea, the lens capsule, the lens and the retina. Optical measurement system 1 includes a main unit 2 which comprises a base 3 and includes many primary subsystems of many embodiments of optical measurement system 1. For example, externally visible subsystems include a touch-screen display control panel 7, a patient interface 4 and a joystick 8.

Patient interface 4 may include one or more structures configured to hold a patient's head in a stable, immobile and comfortable position during the diagnostic measurements while also maintaining the eye of the patient in a suitable alignment with the diagnostic system. In a particularly preferred embodiment, the eye of the patient remains in substantially the same position relative to the diagnostic system for all diagnostic and imaging measurements performed by optical measurement system 1.

In one embodiment patient interface 4 includes a chin support 6 and/or a forehead rest 5 configured to hold the head of the patient in a single, uniform position suitably aligned with respect to optical measurement system 1 throughout the diagnostic measurement. As shown in FIG. 13C, the optical measurement system 1 may be disposed so that the patient may be seated in a patient chair 9. Patient chair 9 can be configured to be adjusted and oriented in three axes (x, y, and z) so that the patient's head can be at a suitable height and lateral position for placement on the patient interface.

In many embodiments, optical measurement system 1 may include external communication connections. For example, optical measurement system 1 can include a network connection (e.g., an RJ45 network connection or WiFi) for connecting optical measurement system 1 to a network. The network connection can be used to enable network printing of diagnostic reports, remote access to view patient diagnostic reports, and remote access to perform system diagnostics. Optical measurement system 1 can include a video output port (e.g., HDMI) that can be used to output video of diagnostic measurements performed by optical measurement system 1. The output video can be displayed on an external monitor for, for example, viewing by physicians or users. The output video can also be recorded for, for example, archival or training purposes. Optical measurement system 1 can include one or more data output ports (e.g., USB) to enable export of patient diagnostic reports to, for example, a data storage device or a computer readable medium, for example a non-volatile computer readable medium, coupled to a laser cataract surgery device for use of the diagnostic measurements in conducting laser cataract surgeries. The diagnostic reports stored on the data storage device or computer readable medium can then be accessed at a later time for any suitable purpose such as, for example, printing from an external computer in the case where the user without access to network based printing or for use during cataract surgery, including laser cataract surgery. Other uses of network data include obtaining service logs, outcomes analysis and algorithm improvement.

Figure 14:
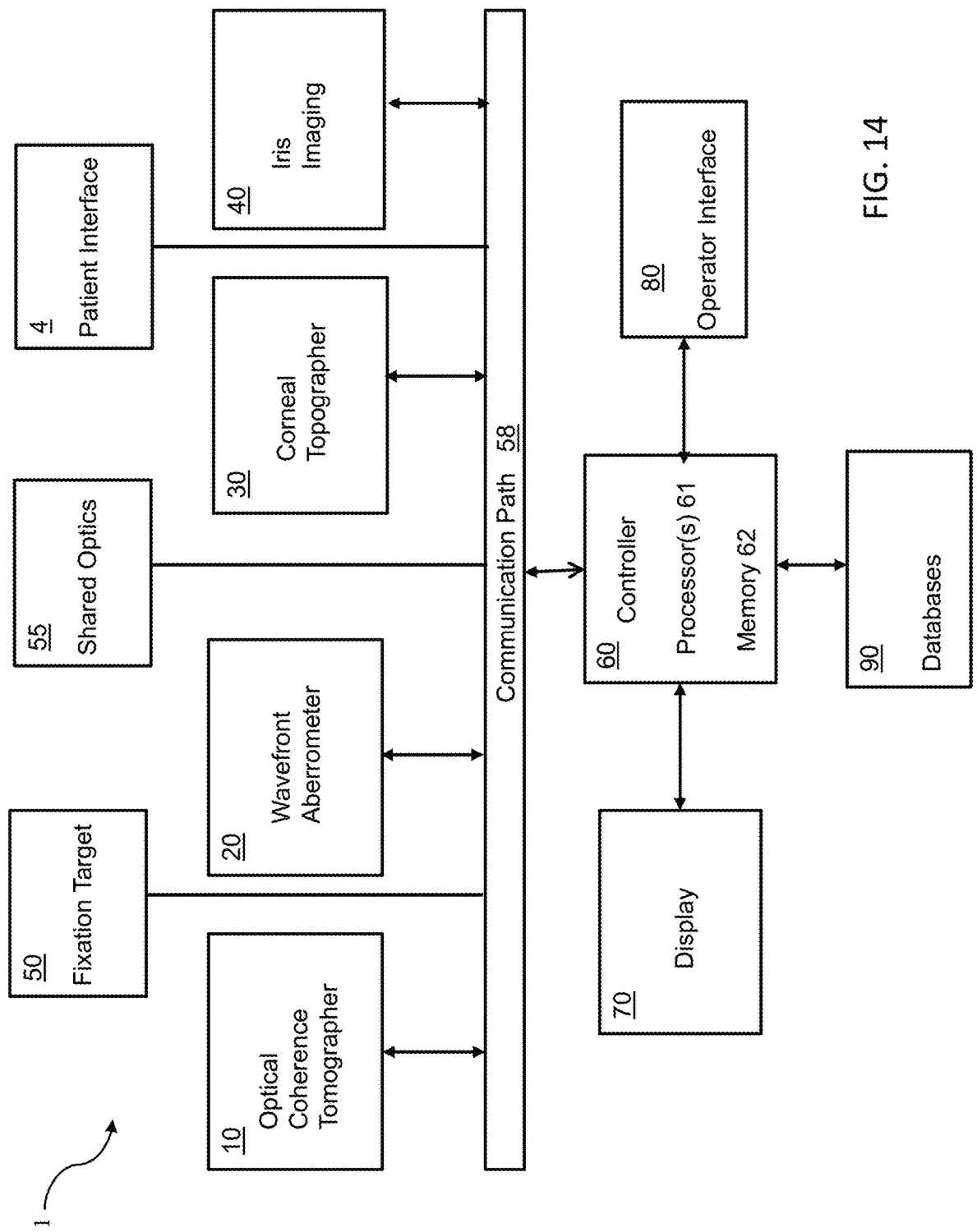
FIG. 14 is a block diagram of a system including an optical measurement instrument, and a position of an eye relative to the system according to one or more embodiments described herein which may be used by the optical measurement.

FIG. 14 is a block diagram of optical measurement system 1 according to one or more embodiments described herein. Optical measurement system 1 includes: an optical coherence tomography (OCT) subsystem 10, a wavefront aberrometer subsystem 20, and a corneal topographer subsystem 30 for measuring one or more characteristics of a subject's eye. Optical measurement system 1 may further include an iris imaging subsystem 40, a fixation target subsystem 50, a controller 60, including one or more processor(s) 61 and memory 62, a display 70 and an operator interface 80. Optical measurement system 1 further includes patient interface 4 for a subject to present his or her eye 101 for measurement by optical measurement system 1.

As noted above, optical coherence tomography subsystem 10 may be configured to measure the spatial disposition (e.g., three-dimensional coordinates such as X, Y, and Z of points on boundaries) of eye structures in three dimensions. Such structure of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, the limbus and/or the retina. The spatial disposition of the structures of interest and/or of suitable matching geometric modeling such as surfaces and curves can be generated and/or used by controller 60 for a number of purposes, including, in some embodiment to program and control a subsequent laser-assisted surgical procedure. The spatial disposition of the structures of interest and/or of suitable matching geometric modeling can also be used to determine a wide variety of parameters. Beneficially, optical coherence tomography subsystem 10 may employ swept source optical coherence tomography (SS-OCT) or spectral domain OCT (SDOCT). In some embodiments, OCT subsystem 10 may include OCT scanning sub system 3000.

Wavefront aberrometer subsystem 20 is configured to measure ocular aberrations, which may include low and high order aberrations, by measuring the wavefront emerging from the eye by, for example a Shack-Hartman wavefront sensor.

Corneal topographer subsystem 30 may apply any number of modalities to measure the shape of the cornea including one or more of a keratometry reading of the eye, a corneal topography of the eye, an optical coherence tomography of the eye, a Placido disc topography of the eye, a reflection of a plurality of points from the cornea topography of the eye, a grid reflected from the cornea of the eye topography, a Hartmann-Shack measurement of the eye, a Scheimpflug image topography of the eye, a confocal tomography of the eye, a Helmholtz source topographer, or a low coherence reflectometry of the eye. The shape of the cornea should generally be measured while the patient is engaged with patient interface 4.

Fixation target subsystem 50 is configured to control the patient's accommodation and alignment direction, because it is often desired to measure the refraction and wavefront aberrations when an eye under measurement is focused at its far point Images captured by corneal topographer subsystem 10, wavefront aberrometer 20, optical coherence tomographer subsystem 30 or camera 40 may be displayed with a display of operator interface 80 or display 70 of optical measurement system 1, respectively. Operator interface 80 may also be used to modify, distort, or transform any of the displayed images.

Shared optics 55 provide a common propagation path that is disposed between patient interface 4 and each of optical coherence tomography (OCT) subsystem 10, wavefront aberrometer subsystem 20, corneal topographer subsystem 30, and in some embodiments, camera 40, and fixation target subsystem 50. In many embodiments, shared optics 55 may comprise a number of optical elements, including mirrors, lenses and beam combiners to receive the emission from the respective subsystem to the patient's eye and, in some cases, to redirect the emission from a patient's eye along the common propagation path to an appropriate director.

Controller 60 controls the operation of optical measurement system 1 and can receive input from any of optical coherence tomographer (OCT) subsystem 10, wavefront aberrometer subsystem 20, corneal topographer subsystem 30 for measuring one or more characteristics of a subject's eye, camera 40, fixation target subsystem 50, display 70 and operator interface 80 via communication paths 58. Controller 60 can include any suitable components, such as one or more processor, one or more field-programmable gate array (FPGA), and one or more memory storage devices. In many embodiments, controller 60 controls display 70 to provide for user control over the laser eye surgery procedure for pre-cataract procedure planning according to user specified treatment parameters as well as to provide user control over the laser eye surgery procedure. Communication paths 58 can be implemented in any suitable configuration, including any suitable shared or dedicated communication paths between controller 60 and the respective system components.

Operator interface 80 can include any suitable user input device suitable to provide user input to controller 60. For example, user interface devices 80 can include devices such as joystick 8, a keyboard, or a touchscreen display.

Figure 15A:
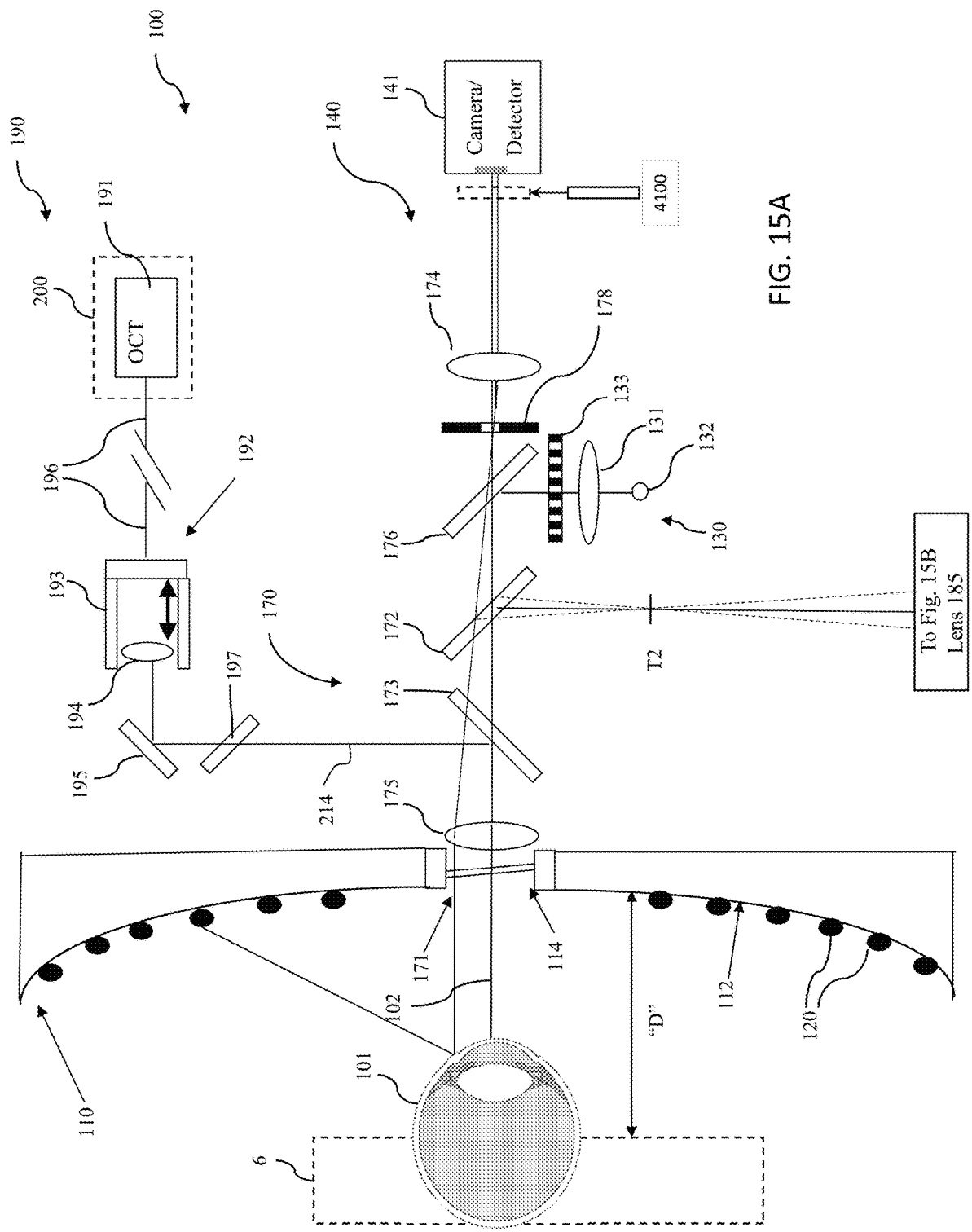
FIGS. 15A and 15B illustrate together an assembly illustrating a suitable configuration and integration of an optical coherence tomographer subsystem, a wavefront aberrometer subsystem, a corneal topographer subsystem, an iris imaging subsystem, a fixation target subsystem according to a non-limiting embodiment of the present invention.
Figure 15B:
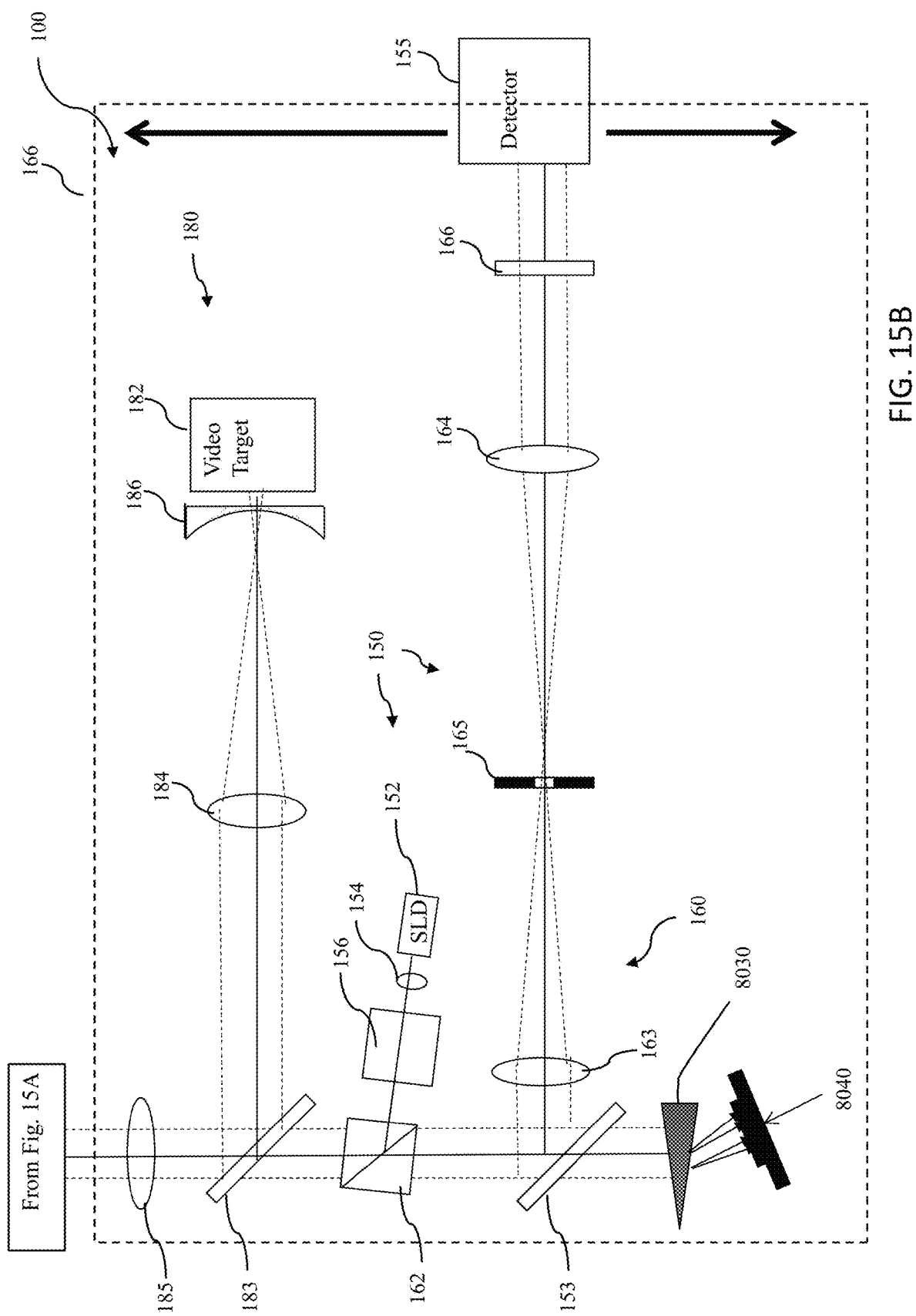

FIGS. 15A and 15B are simplified block diagrams illustrating an assembly 100 according to many embodiments which may be included in optical measurement system 1. Assembly 100 is a non-limiting example of suitable configurations and integration of an optical coherence tomography (OCT) subsystem 190, a wavefront aberrometer subsystem 150, a corneal topographer subsystem 140 for measuring one or more characteristics of a subject's eye 101, camera 40, a fixation target subsystem 180 and shared optics.

The shared optics generally comprise one or more components of a first optical system 170 disposed along a central axis 102 passing through the opening or aperture 114 of the structure 110. First optical system 170 directs light from the various light sources along the central axis 102 towards an eye 101 and establishes a shared or common optical path along which the light from the various light sources travel to eye 101. In one embodiment, optical system 170 comprises a quarter wave plate 171, a first beamsplitter 172, a second beamsplitter 1715, an optical element (e.g., a lens) 174, a lens 1710, a third beamsplitter 176, and a structure including an aperture 178. Additional optical systems may be used in assembly 100 to direct light beams from one or more light sources to the first optical system 170. For example, a second optical system 160 directs light to the first optical system 170 from wavefront aberrometer subsystem 150 and comprises mirror 153, beam splitter 183 and lens 185.

Other configurations of assembly 100 may be possible and may be apparent to a person of skill in the art.

Corneal topographer subsystem 140 comprises a structure 110 having a principal surface 112 with an opening or aperture 114 therein; a plurality of first (or peripheral) light sources 120 provided on the principal surface 112 of structure 110; a Helmholz light source 130; and a detector, photodetector, or detector array 141, for example a camera.

In one embodiment, structure 110 has the shape of an elongated oval or "zeppelin" with openings or apertures at either end thereof. An example of such a structure is disclosed in Yobani Meji'a-Barbosa et al., "Object surface for applying a modified Hartmann test to measure corneal topography," APPLIED OPTICS, Vol. 40, No. 31 (Nov. 1, 2001) ("Meji'a-Barbosa"). In some embodiments, principal surface 112 of structure 110 is concave when viewed from the cornea of eye 101, as illustrated in FIG. 15A.

In one embodiment where principal surface 112 is concave, principal surface 112 has the shape of a conical frustum. Alternatively, principal surface 112 may have a shape of hemisphere or some other portion of a sphere, with an opening or aperture therein. Also alternatively, principal surface 112 may have the shape of a modified sphere or conical frustum, with a side portion removed. Beneficially, such an arrangement may improve the ergonomics of assembly 100 by more easily allowing structure 110 to be more closely located to a subject's eye 101 without being obstructed by the subject's nose. Of course, a variety of other configurations and shapes for principal surface 112 are possible.

In the embodiment of FIG. 15A, the plurality of first light sources 120 are provided on the principal surface 112 of structure 110 so as to illuminate the cornea of eye 101. In one embodiment, light sources 122 may comprise individual light generating elements or lamps, such as light emitting diodes (LEDs) and/or the tips of the individual optical fibers of a fiber bundle. Alternatively, principal surface 112 of structure 110 may have a plurality of holes or apertures therein, and one or more backlight lamps, which may include reflectors and/or diffusers, may be provided for passing lighting through the holes to form the plurality of first light sources 120 which project light onto the cornea of eye 101. Other arrangements are possible.

In another embodiment, structure 110 is omitted from assembly 100, and the first light sources 120 may be independently suspended (e.g., as separate optical fibers) to form a group of first light sources 120 arranged around a central axis, the group being separated from the axis by a radial distance defining an aperture in the group (corresponding generally to the aperture 114 in the structure 110 illustrated in FIG. 15A).

In operation, a ray (solid line) from one of the first light sources 120 is reflected by the cornea and passes through optical system 170, to appear as a light spot on detector array 141. It will be appreciated that this ray is representative of a small bundle of rays that make it through optical system 170 and onto detector array 141, all of which will focus to substantially the same location on detector array 141. Other rays from that first light source 120 are either blocked by the aperture 178 or are otherwise scattered so as to not pass through the optical system 170. In similar fashion, light from the other first light sources 120 are imaged onto detector array 141 such that each one of first light sources 120 is imaged or mapped to a location on detector array 141 that may be correlated to a particular reflection location on the cornea of eye 101 and/or the shape of the cornea. Thus, detector array 141 detects the light spots projected thereon and provides corresponding output signals to a processor of controller 60 (FIG. 7). The processor determines the locations and/or shape of the light spots on detector array 141, and compares these locations and/or shapes to those expected for a standard or model cornea, thereby allowing the processor of controller 60 to determine the corneal topography. Alternatively, other ways of processing the spot images on detector array 141 may be used to determine the corneal topography of eye 101, or other information related to the characterization of eye 101.

Detector array 141 comprises a plurality of light detecting elements arranged in a two dimensional array. In one embodiment, detector array 141 comprises such a charge-coupled device (CCD), such as may be found in a video camera. However, other arrangements such as a CMOS array, or another electronic photosensitive device, may be employed instead. Beneficially, the video output signal(s) of detector array 141 are provided to processor 60 which processes these output signals as described in greater detail below.

Assembly 100 also comprises a Helmholtz light source 130 configured according to the Helmholtz principle. As used herein, the term "Helmholtz source" or "Helmholtz light source" means one or a plurality of individual light sources disposed such that light from each of the individual light sources passes through an optical element having optical power, reflects off of a reference or test object, passes through the optical element, and is received by a detector, wherein light from the Helmholtz source is used to determine geometric and/or optical information of at least a portion of a surface of the reference or test object. In general, it is a characteristic of Helmholtz sources that the signal at the detector is independent of the relative position of the test or reference object relative to the Helmholtz source. As used herein, the term "optical element" means an element that refracts, reflects, and/or diffracts light and has either positive or negative optical power.

In such embodiments, the Helmholtz light source 130 is located at optical infinity with respect to eye 101. The Helmholtz principle includes the use of such infinite sources in combination with a telecentric detector system: i.e., a system that places the detector array at optical infinity with respect to the surface under measurement, in addition to insuring that the principal measured ray leaving the surface is parallel to the optical axis of the instrument. The Helmholtz corneal measurement principle has the Helmholtz light source at optical infinity and the telecentric observing system so that detector array 141 is also optically at an infinite distance from the images of the sources formed by the cornea. Such a measurement system is insensitive to axial misalignment of the corneal surface with respect to the instrument.

In one embodiment, the Helmholtz light source 130 comprises a second light source 132 which may comprise a plurality of lamps, such as LEDs or optical fiber tips. In one embodiment, second light source 132 comprises an LED and a plate 133 with plurality of holes or apertures in a surface that are illuminated by one or more backlight lamps with an optical element 131, which may comprise diffusers.

In one embodiment, lamps of second light sources 132 are located off the central optical axis 102 of assembly 100, and light from second light sources 132 is directed toward optical element 171 by third beamsplitter 176.

The operation of the topographer portion of assembly 100 may be conducted with the combined use of first light source 120 and the Helmholz light source 130. In operation, detector array 141 detects the light spots projected thereon from both Helmholz light source 130 (detected at a central portion of detector array 141) and first light sources 120 (detected at a peripheral portion of detector array 141) and provides corresponding output signals to processor. In general, the images of first light sources 120 that appear on detector array 141 emanate from an outer region of the surface of the cornea, and the images of Helmholz light source 130 that appear on detector array 141 emanate from a central or paraxial region of the surface of the cornea. Accordingly, even though information about the central region of the corneal surface (e.g., surface curvature) cannot be determined from the images of first light sources 120 on detector array 141, such information can be determined from the images of Helmholz light source 130 on detector array 141. A processor of controller 60 determines the locations and/or shapes of the light spots on detector array 141, and compares these locations and/or shapes to those expected based for a standard or model cornea, thereby allowing the processor to determine the corneal topography of eye 101. Accordingly, the topography of the entire corneal surface can be characterized by assembly 100 without a "hole" or missing data from the central corneal region.

As seen in FIG. 15B, assembly 100 also includes spectrally dispersive element 8030 and a second two-dimensional detector array 8040. Although not shown in FIGS. 15A and 15B, instead of elements 8030 and 8040, assembly 100 may include elements of apparatus 10000, for example including broadband light source 10010, a frequency tunable, or scanning, filter 10020, and optical fibers 10030.

In some embodiments, contemporaneous with obtaining the eye measurement data (e.g., wavefront aberrometry data and/or corneal topographer data) for eye 101, an image of sclera 408 of eye 101 may be captured by detector array 141. The image may be processed by a processor (e.g., processor 61 of controller 60) executing a pattern recognition algorithm as known in the art to identify unique features of sclera 408, for example scleral blood vessels. Processor 61 may execute a pattern recognition algorithm as a set of computer instructions stored in a memory (e.g., memory 62) associated with processor 61. Processor 61 may use the identified features from the image of eye 101 as fiducials or registration markers for the eye measurement data for eye 101. In some embodiments, processor 61 may store in memory 62 the eye measurement data (e.g., wavefront aberrometry data and/or corneal topographer data), a first image of eye 101 focused at the appropriate image plane for the eye measurement data (e.g., focused at iris 404 for wavefront measurement data), a second image of eye 101 focused at the fiducials (e.g., scleral blood vessels), and registration data which registers the eye measurement data to the locations of the identified features or fiducials in the image of eye 101. This set of data may be used by a surgical instrument in a subsequent surgery. For example, the surgical instrument may include a camera which is able to capture an image of eye 101, including the fiducials. By mapping the fiducials identified by assembly 100 to the same fiducials observed by the camera of the surgical instrument, the eye measurement data may be registered to the locations of the fiducials observed by the camera of the surgical instrument via the registration data of assembly 100.

Wavefront aberrometer subsystem 150 of assembly 100 comprises a third light source 152 providing a probe beam and a wavefront sensor 155. Wavefront aberrometer subsystem 150 preferably further comprises a collimating lens 154, a polarizing beamsplitter 156, an adjustable telescope comprising a first optical element, lens 163 and a second optical element, lens 164, a movable stage or platform 166, and a dynamic-range limiting aperture 165 for limiting a dynamic range of light provided to wavefront sensor 155 so as to preclude data ambiguity. Light from the wavefront aberrometer subsystem is directed to one of the constituent optical elements of the optical system 170 disposed along a central axis 102 passing through the opening or aperture 114 of the structure 110. It will be appreciated by those of skill in the art that the lenses 163, 164, or any of the other lenses discussed herein, may be replaced or supplemented by another type of converging or diverging optical element, such as a diffractive optical element.

Light source 152 may be an 840 nm SLD (super luminescent laser diode). An SLD is similar to a laser in that the light originates from a very small emitter area. However, unlike a laser, the spectral width of the SLD is very broad, about 40 nm. This tends to reduce speckle effects and improve the images that are used for wavefront measurements.

Beneficially, wavefront sensor 155 may be a Shack-Hartmann wavefront sensor comprising a detector array and a plurality of lenslets for focusing received light onto its detector array. In that case, the detector array may be a CCD, a CMOS array, or another electronic photosensitive device. However, other wavefront sensors may be employed instead. Embodiments of wavefront sensors which may be employed in one or more systems described herein are described in U.S. Pat. No. 6,550,917, issued to Neal et al. on Apr. 22, 2003, and U.S. Pat. No. 5,777,719, issued to Williams et al. on Jul. 7, 1998, both of which patents are hereby incorporated herein by reference in their entirety.

The aperture or opening in the middle of the group of first light sources 120 (e.g., aperture 114 in principal surface 112 of structure 110) allows assembly 100 to provide a probe beam into eye 101 to characterize its total ocular aberrations. Accordingly, third light source 152 supplies a probe beam through a light source polarizing beam splitter 156 and polarizing beam splitter 162 to first beamsplitter 172 of optical system 170. First beamsplitter 172 directs the probe beam through aperture 114 to eye 101. Preferably, light from the probe beam is scattered from the retina of eye 101, and at least a portion of the scattered light passes back through aperture 114 to first beamsplitter 172. First beamsplitter 172 directs the back scattered light back through beam splitter 172 to polarizing beamsplitter 162, mirror 153 to wavefront sensor 155.

Wavefront sensor 155 outputs signals to a processor of controller 60 which uses the signals to determine ocular aberrations of eye 101. Preferably, the processor is able to better characterize eye 101 by considering the corneal topography of eye 101 measured by corneal topography subsystem 140, which may also be determined by the processor based on outputs of detector array 141, as explained above.

In operation of wavefront aberrometer subsystem 150, light from light source 152 is collimated by lens 154. The light passes through light source polarizing beam splitter 156. The light entering light source polarizing beam splitter 156 is partially polarized. Light source polarizing beam splitter 156 reflects light having a first, S, polarization, and transmits light having a second, P, polarization so the exiting light is 100% linearly polarized. In this case, S and P refer to polarization directions relative to the hypotenuse in light source polarizing beam splitter 156.

Light from light source polarizing beam splitter 156 enters polarizing beamsplitter 162. The hypotenuse of polarizing beamsplitter 162 is rotated 90 degrees relative to the hypotenuse of light source polarizing beamsplitter 156 so the light is now S polarized relative the hypotenuse of polarizing beamsplitter 162 and therefore the light reflects upwards. The light from polarizing beamsplitter 162 travels upward and passes through toward beam splitter 172, retaining its S polarization, and then travels through quarter wave plate 171. Quarter wave plate 171 converts the light to circular polarization. The light then travels through aperture 114 in principal surface 112 of structure 110 to eye 101. Preferably, the beam diameter on the cornea is between 1 and 2 mm. Then the light travels through the cornea and focuses onto the retina of eye 101.

The focused spot of light becomes a light source that is used to characterize eye 101 with wavefront sensor 155. Light from the probe beam that impinges on the retina of eye 101 scatters in various directions. Some of the light reflects back as a semi-collimated beam back towards assembly 100. Upon scattering, about 90% of the light retains its polarization. So the light traveling back towards assembly is substantially still circularly polarized. The light then travels through aperture 114 in principal surface 112 of structure 110, through quarterwave plate 171, and is converted back to linear polarization. Quarterwave plate 171 converts the polarization of the light from the eye's retina so that it is P polarized, in contrast to probe beam received from third light source 150 having the S polarization. This P polarized light then reflects off of first beamsplitter 172, and then reaches polarizing beamsplitter 162. Since the light is now P polarized relative the hypotenuse of polarizing beamsplitter 162, the beam is transmitted and then continues onto mirror 153. After being reflected by mirror 153, light is sent to an adjustable telescope comprising a first optical element 164 and a second optical element (e.g., lens) 163 and a movable stage or platform 166. The beam is also directed through a dynamic-range limiting aperture 165 for limiting a dynamic range of light provided to wavefront sensor 155 so as to preclude data ambiguity.

When wavefront sensor 155 is a Shack-Hartmann sensor, the light is collected by the lenslet array in wavefront sensor 155 and an image of spots appears on the detector array (e.g., CCD) in wavefront sensor 155. This image is then provided to a processor of controller 60 and analyzed to compute the refraction and aberrations of eye 101.

OCT subsystem 190 of assembly 100 may comprise an OCT assembly 191, and a third optical path 192 which directs the OCT beam of the OCT light source to the first optical path 170. The third optical path 192 may comprise a fiber optic line 196, for conducting the OCT beam from the OCT light source of OCT assembly 191, a Z-scan device 193 operable to alter the focus of the beam in the Z-direction (i.e., along the direction of propagation of the OCT beam) under control of the controller, and X-scan device 195, and a Y-scan device 197 operable to translate the OCT beam in the X and Y directions (i.e., perpendicular to the direction of propagation of the of the OCT beam), respectively, under control of controller 60. The OCT light source and reference arm may be incorporated into assembly 100 of optical measurement system 1 shown in FIG. 15A. Alternatively, OCT assembly 191 may be housed in a second unit or housing 200 and the OCT beam from the OCT source may be directed from second unit 200 to the main unit by optical pathway 192.

Beneficially, the OCT systems and methods employed in optical measurement system 1 and assembly 100 may employ swept source optical coherence tomography (SS-OCT) as described above. Beneficially, optical measurement system 1, assembly 100 and OCT subsystem 190 may each comprise OCT interferometer 1000, 3000 or 4000.

As explained above, in SS-OCT, a rapid-scanning laser source is employed. By rapidly sweeping the source wavelength over a broad wavelength range, and collecting all the scattering and reflection information at each wavelength and at each position, the collected spectral data may be inverse-Fourier-transformed to recover the spatial depth-dependent information for the object under test (e.g., eye 101).

In operation, as shown in FIG. 15A, after exiting connector 212, OCT probe beam 214 may be collimated, for example using a collimating optical fiber 196. Following collimating fiber 196 OCT probe beam 214 is optionally directed to Z-scan device 193 operable to change the focal point of OCT probe beam 214 in the Z-direction, and X- and Y-scan devices 195 and 197, which are operable to scan the OCT beam in X and Y-directions perpendicular to the Z-direction.

Following the collimating optical fiber 196, OCT probe beam 214 continues through a Z-scan device 193. Z-scan device 193 may comprise a Z-telescope 194 which is operable to scan focus position of OCT probe beam 214 in the patient's eye 101 along the Z axis. For example, Z-telescope 194 may include a Galilean telescope with two lens groups (each lens group includes one or more lenses). One of the lens groups moves along the Z axis about the collimation position of Z-scan device 193. In this way, the focus position in the patient's eye 101 moves along the Z axis. In general, there is a relationship between the motion of lens group and the motion of the focus point. The exact relationship between the motion of the lens and the motion of the focus in the Z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. Z-telescope 194 functions as a Z-scan device for changing the focus point of OCT probe beam 214 in patient's eye 101. Z-scan telescope 194 can be controlled automatically and dynamically by controller 60 and selected to be independent or to interplay with X and Y scan devices 195 and 197.

After passing through the z-scan device, the OCT probe beam 214 is incident upon an X-scan device 195, which is operable to scan the OCT probe beam 214 in the X direction, which is dominantly transverse to the Z axis and transverse to the direction of propagation of OCT probe beam 214. X-scan device 195 is controlled by controller 60, and can include suitable components, such as a lens coupled to a MEMS device, a motor, galvanometer, or any other well-known optic moving device. The relationship of the motion of OCT probe beam 214 as a function of the motion of the actuator of X-scan device 195 does not have to be fixed or linear. Modeling or calibrated measurement of the relationship or a combination of both can be determined and used to direct the location of OCT probe beam 214.

After being directed by the X-scan device 195, OCT probe beam 214 is incident upon a Y scan device 197, which is operable to scan OCT probe beam 214 in the Y direction, which is dominantly transverse to the X and Z axes. Y-scan device 197 is controlled by the controller 60, and can include suitable components, such as a lens coupled to a MEMS device, motor, galvanometer, or any other well-known optic moving device. The relationship of the motion of the beam as a function of the motion of the Y actuator of Y-scan device 197 does not have to be fixed or linear. Modeling or calibrated measurement of the relationship or a combination of both can be determined and used to direct the location of OCT probe beam 214. Alternatively, the functionality of X-Scan device 195 and Y-Scan device 197 can be provided by an XY-scan device configured to scan OCT probe beam 214 in two dimensions transverse to the Z axis and the propagation direction of OCT probe beam 214. The X-scan and Y scan devices 195, 197 change the resulting direction of OCT probe beam 214, causing lateral displacements of OCT probe beam 214 located in the patient's eye 101.

OCT probe beam 214 is then directed to beam splitter 1715 through lens 1720, and thence through lens 1710, quarter wave plate 171 and aperture 114 and to the patient eye 101. Reflections and scattering off of structures within the eye provide return beams that retrace back through the patient interface quarter wave plate 171, lens 1710, beam splitter 1715, lens 1720, Y-scan device 197, X-scan device 195, Z-scan device 193, optical fiber 196 and beam combiner 204, and back into the OCT detection device. The returning back reflections of the sample arm are combined with the returning reference portion and directed into the detector portion of the OCT detection device, which generates OCT signals in response to the combined returning beams. The generated OCT signals that are in turn interpreted by controller 60 to determine the spatial disposition of the structures of interest in patient's eye 101. The generated OCT signals can also be interpreted by the controller to determine the spatial disposition of the structures of interest in the patient's eye 101. The generated OCT signals can also be interpreted by the control electronics to align the position and orientation of the patient eye 101 within patient interface 4.

Optical measurement systems disclosed herein may comprise an iris imaging subsystem 40. Iris imaging subsystem 40 generally may comprise an infrared light source, for example an infrared light source 152, and detector 141. In operation light from light source 152 is directed along second optical path 160 to first optical path 170 and is subsequently directed to eye 101 as described above. Light reflected from the iris of eye 101 is reflected back along first optical path 170 to detector 141. In normal use, an operator will adjust a position or alignment of system 100 in X, Y and Z directions to align the patient according to the image detector array 141. In one embodiment of the iris imaging subsystem, eye 101 is illuminated with infrared light from light source 152. In this way, the wavefront obtained by wavefront sensor 155 will be registered to the image from detector array 141.

The image that the operator sees is the iris of eye 101. The cornea generally magnifies and slightly displaces the image from the physical location of the iris. So the alignment that is done is actually to the entrance pupil of the eye. This is generally the desired condition for wavefront sensing and iris registration.

Iris images obtained by the iris imaging subsystem may be used for registering and/or fusing the multiple data sets obtained by the various subsystems of optical measurement system 1 by methods described, for instance, in "Method for registering multiple data sets," U.S. patent application Ser. No. 12/418,841, which is incorporated herein by reference.

As set forth in application Ser. No. 12/418,841, wavefront aberrometry may be fused with corneal topography, optical coherence tomography and wavefront, optical coherence tomography and topography, pachymetry and wavefront, etc. For instance, with image recognition techniques it is possible to find the position and extent of various features in an image. Regarding iris registration images, features that are available include the position, size and shape of the pupil, the position, size and shape of the outer iris boundary (OIB), salient iris features (landmarks) and other features as are determined to be needed. Using these techniques, patient movement between measurements (and/or during a measurement sequence) can be identified, as well as changes in the eye itself (including those induced by the measurement, such as changes in the size of the pupil, changes in pupil location, etc.).

In many embodiments, optical measurement system 1 includes fixation target subsystem 50 (FIG. 14), and accordingly assembly 100 shown in FIGS. 15A and 15B includes fixation target subsystem 180 which includes a fixation target 182 for the patient to view. Fixation target subsystem 180 is used to control the patient's accommodation and alignment, because it is often desired to measure the refraction and wavefront aberrations when eye 101 is focused at its far point (e.g., because LASIK treatments are primarily based on this). In fixation target subsystem 180, a projection of a target, for instance a cross-hair pattern is projected onto eye 101 of the patient, the cross hair pattern being formed, e.g. by fixation target 182 comprising a backlit LED and a film.

In operation, light originates from fixation target 182 and lenses 186 and 184. Lens 185 collects the light and forms an aerial image T2. This aerial image T2 is the one that the patient views. The patient focus is maintained on aerial image T2 during measurement so as to maintain the eye in a fixed focal position. In some embodiments, fixation target 182 may comprise a video target which may have a variable center location under control of one or more processors 61 of controller 60, for example a blinking dot which may cause aerial image T2 to appear at a plurality of different angular locations (e.g., five different angular locations) relative to eye 101. In this case, the patient may be instructed to gaze at the blinking dot as it moves from location to location to create a plurality of different gaze angles for eye 101. Accordingly, optical coherence tomography subsystem 10 may collect OCT data sets for retina 409 for each of the plurality of gaze angles, e.g., five different gaze angles, causing five different regions of retina 409 to be sampled. In that way, in some embodiments the total combined scanned diameter retina 409 could be expanded from 3 mm to a larger region with a diameter of approximately 6 mm, providing a larger area of retina 409 from which retinal health may be evaluated.

The operating sequence the optical measurement system and methods of the present is not particularly limited. A scan of the patient's eye may comprise one or more of a wavefront aberrometry measurement of a patient's eye utilizing the wavefront aberrometry subsystem, a corneal topography measurement of a patient's eye and an OCT scan of the patient's eye using the OCT subsystem, wherein the OCT scan includes a scan at each or one or more locations within the eye of the patient. These locations of the OCT scan may correspond to the location of the cornea, the location of the anterior portion of the lens, the location of the posterior portion of the lens and the location of the retina. In a preferred embodiment, the operating sequence includes each of a wavefront aberrometry measurement, a corneal topography measurement and an OCT scan, wherein the OCT scan measures at least the locations of the retina, the cornea and one of anterior portion of the patient's lens. An iris image may be taken simultaneously with or sequentially with each of the measurements taken with wavefront aberrometry subsystem, the corneal topography subsystem and the OCT subsystem, including an iris image take simultaneously with or sequentially with the location of each OCT scan. This results in improved accuracy in the 3-dimensional modeling of the patient's eye by permitting the various data sets to be fused and merged into a 3-dimensional model.

Optical measurement system 1 and the optical measurements obtained therewith may be used pre-operatively, i.e. before a cataract surgery or other surgical procedure, for, e.g., eye biometry and other measurements, diagnostics and surgical planning. Surgical planning may include one or more predictive models. In the one or more predictive models, one or more characteristics of the postoperative condition of the patient's eye or vision is modeled based on one or more selected from the group consisting of pre-operative measurements obtained from the optical measurement system 1, a contemplated surgical intervention, and on or more algorithms or models stored in the memory of the optical measurement system 1 and executed by the processor. The contemplated surgical intervention may include the selection of an IOL for placement, the alignment of a toric IOL in the eye, the selection of an IOL characteristic, the nature or type of incision to be used during surgery (e.g., relaxation incision), or one or more post-operative vision characteristics requested by the patient.

Optical measurement system 1 and the optical measurements obtained therewith may be used intra-operatively, i.e., during a cataract surgery or other surgical procedure, for, e.g., intraoperative eye diagnostics, determining IOL placement and position, surgical planning, and control/or of a laser surgical system. For instance, in the case of laser cataract surgical procedure, any measurement data obtained preoperatively by the optical measurement instrument may be transferred to a memory associated with a cataract laser surgical system for use before, during or after either the placement of a capsulotomy, fragmentation or a patient's lens or IOL placement during the cataract surgery. In some embodiments, measurements using optical measurement system 1 may be taken during the surgical procedure to determine whether the IOL is properly placed in the patient's eye. In this regard, conditions measured during the surgical procedure may be compared to a predicted condition of the patient's eye based on pre-operative measurements, and a difference between the predicted condition and the actual measured condition may be used to undertake additional or corrective actions during the cataract surgery or other surgical procedure.

Optical measurement system 1 and the optical measurements obtained therewith may be used postoperatively, i.e., after a cataract surgery or other surgical procedure, for, e.g., post-operative measurement, postoperative eye diagnostics, postoperative IOL placement and position determinations, and corrective treatment planning if necessary. The postoperative testing may occur sufficiently after the surgery that the patient's eye has had sufficient time to heal and the patient's vision has achieved a stable, postsurgical state. A postoperative condition may be compared to one or more predicted condition performed pre-operatively, and a difference between the preoperatively predicted condition and the postoperatively measured condition may be used to plan additional or corrective actions during the cataract surgery or other surgical procedure.

Optical measurement system 1, including the corneal topography subsystem, the OCT subsystem and the wavefront aberrometry subsystem, utilizing a suitable operating sequence as disclosed herein, is operable to measure one, more than one or all of the following: ocular biometry information, anterior corneal surface information, posterior corneal surface information, anterior lens surface information, posterior lens surface information, lens tilt information and lens position information. In some embodiments, the ocular biometry information may include a plurality of central corneal thicknesses (CCT), an anterior chamber depth (ACT), a pupil diameter (PD), a white to white distance (WTW), a lens thickness (LT), an axial length (AL) and a retinal layer thickness. This measurement data may be stored in memory 62 associated with controller 60. The plurality of characteristics may be measured preoperatively, and where appropriate, intra-operatively, and postoperatively.

In some embodiments, memory 62 associated with controller 60 may store intraocular lens (IOL) model data for a plurality of IOL models, each of the IOL models having associated with it a plurality of predetermined parameters selected from the group consisting of dioptic power, refractive index, asphericity, toricity, haptic angulation and lens filter. The IOL data may be used by one or more processors of optical measurement system 1, in conjunction with measurement data of a subject's eye obtained by optical measurement system 1, for cataract diagnostics or cataract treatment planning, which may include specifying and/or selecting a particular IOL for a subject's eye. For example, one or more processors of optical measurement system 1 may execute an algorithm which includes: accessing the plurality of IOL models stored in, and for each of the IOL models: (1) modeling the subject's eye with an intraocular lens corresponding to the IOL model and the measured characteristics of the subject's eye; (2) simulating the subject's eye based on the plurality of IOL predetermined parameters and the predicted IOL position; (3) performing one of a ray tracing and a power calculation based on said model of the subject's eye; and (4) selecting an IOL for the subject's eye from the plurality of IOL models corresponding to the optimized IOL based on a predetermined criteria.

In some embodiments, one or more processors of optical measurement system 1 may execute an algorithm comprising: determining a desired postoperative condition of the subject's eye; empirically calculating a post-operative condition of the eye based at least partially on the measured eye characteristics; and predictively estimating, in accordance with an output of said empirically calculating and the eye characteristics, at least one parameter of an intraocular lens for implantation into the subject's eye to obtain the desired postoperative condition.

In many embodiments, the eye imaging and diagnostic system further comprises a memory operable to store Intraocular Lens ("IOL") Data, the IOL data including a plurality of dioptic power, anterior and posterior radius, IOL thickness, refractive index, asphericity, toricity, echelette features, haptic angulation and lens filter.

In many embodiments, the eye imaging and diagnostic system further comprises a memory operable to store intraocular lens ("IOL") model data for a plurality of IOL models, IOL model having associated with a plurality of predetermined parameters selected from the group consisting of dioptic power, anterior and posterior radius, IOL thickness, refractive index, asphericity, toricity, echelette features, haptic angulation and lens filter.

An improved system for selecting an intraocular lens (IOL) for implantation, may comprise: a memory operable to store data acquired from each of the corneal topography subsystem, the wavefront sensor subsystem and the Optical Coherence Tomography subsystem, wherein the stored data includes a plurality of ocular biometry information, anterior corneal surface information, posterior corneal surface information, anterior lens surface information, and posterior lens surface information, lens tilt information and lens position information; the memory further operable to store intraocular lens ("IOL") model data for a plurality of IOL models, IOL model having associated with it a plurality of predetermined parameters selected from the group consisting of dioptic power, anterior and posterior radius, IOL thickness, refractive index, asphericity, toricity, echelette features, haptic angulation and lens filter; and a processor coupled to the memory, the processor deriving the treatment of the eye of the patient applying, for each of the plurality of identified IOL Model, to: (1) predict a position of one of the identified IOL Models when implanted in the subject eye, based on the plurality of characteristics; (2) simulate the subject eye based on the plurality of IOL predetermined parameters and the predicted IOL position; (3) perform one or more of ray tracing and a IOL spherical equivalent (SE) and cylinder (C) power calculation, as well as optionally, to determine the optimum IOL orientation based on said eye model; and (4) propose one IOL power for one or more IOL models from the plurality of IOLs corresponding to the optimized IOL(s) based on predetermined criteria; and (5) show the simulated optical quality and/or visual performance provided by each of the proposed IOL models for distance and/or for any other vergence.

A method of selecting an intraocular lens (IOL) to be implanted in a subject's eye, may comprise: measuring a plurality of eye characteristics comprising ocular biometry information, anterior corneal surface information, posterior corneal surface information, anterior lens surface information, and posterior lens surface information, lens tilt information and lens position information; and for each of Intraocular Lens ("IOL") model having associated with it a plurality of predetermined parameters selected from the group consisting of dioptic power, refractive index, anterior and posterior radius, IOL thickness, asphericity, toricity, echelette design, haptic angulation and lens filter: (1) modeling the subject eye with the intraocular lens; (2) simulating the subject eye based on the plurality of IOL predetermined parameters and the predicted IOL position; (3) performing a ray tracing and a IOL spherical equivalent (SE) and cylinder (C) power calculation, as well as determine the optimum IOL orientation based on said eye model; and (4) proposing one IOL power for one or more IOL models from the plurality of IOLs corresponding to the optimized IOL(s) based on predetermined criteria; and optionally (5) show the simulated optical quality and/or visual performance provided by each of the proposed IOL models for distance and/or for any other vergence.

A tangible computer-readable storage device may store computer instructions which, when read by a computer, cause the computer to perform a method comprising: receiving a plurality of eye characteristics comprising ocular biometry information, anterior corneal surface information, posterior corneal surface information, anterior lens surface information, and posterior lens surface information, lens tilt information and lens position information; for each of Intraocular Lens ("IOL") model having associated with it a plurality of predetermined parameters selected from the group consisting of dioptic power, refractive index, anterior and posterior radius, IOL thickness, asphericity, toricity, echelette design, haptic angulation and lens filter: (1) simulating a geometry of the subject eye with each of the plurality of intraocular lenses (IOL) implanted, in accordance with the plurality of eye characteristics; (2) performing a ray tracing and a IOL spherical equivalent (SE) and cylinder (C) power calculation, as well as optionally determining the optimum IOL orientation based on said eye model; (3) proposing one IOL power for one or more IOL models from the plurality of IOLs corresponding to the optimized IOL(s) based on predetermined criteria; and optionally (4) showing the simulated optical quality and/or visual performance provided by each of the proposed IOL models for distance and/or for any other vergence.

A method of predicting the intraocular lens position may comprise: determining a plurality of eye characteristics before cataract surgery, comprising ocular biometry information, anterior corneal surface information, posterior corneal surface information, anterior lens surface information, and posterior lens surface information, lens tilt information and lens position information; determining a plurality of eye characteristics after cataract surgery, comprising ocular biometry information, anterior corneal surface information, posterior corneal surface information, anterior lens surface information, and posterior lens surface information, lens tilt information and lens position information; calculating or measuring, based on a mathematical relationship, a distance from the apex to a plane of the intraocular lens after an ocular surgical procedure; calculating an optical power of the intraocular lens suitable for providing a predetermined refractive outcome; wherein a mathematical relationship is found between the preoperative and postoperative eye characteristics that accurately predict the measured distance from the apex to the plane where the intraocular lens is.

An improved system for planning a refractive treatment of an eye of a patient, may comprise: a memory operable to store eye measurement data comprising ocular biometry information, anterior corneal surface information, posterior corneal surface information, anterior lens surface information, and posterior lens surface information, lens tilt information and lens position information; a processor coupled to the memory, the processor deriving the treatment of the eye of the patient applying an effective treatment transfer function, wherein the effective treatment transfer function is derived from, for each of a plurality of prior eye treatments, a correlation between a pre-treatment vector characterizing the eye measurement data before treatment, and a post-treatment vector characterizing post-treatment eye measurement data of the associated eye; an output coupled to the processor so as to transmit the treatment to facilitate improving refraction of the eye of the patient. The processor may comprise tangible media embodying machine readable instructions for implementing the derivation of the treatment.

An improved method for planning a refractive treatment of an eye of a patient may comprise: measuring a plurality of ocular biometry information, anterior corneal surface information, posterior corneal surface information, anterior lens surface information, and posterior lens surface information, lens tilt information and lens position information.

A method of customizing at least one parameter of an intraocular lens, may comprise: measuring a plurality of eye characteristics comprising ocular biometry information, anterior corneal surface information, posterior corneal surface information, anterior lens surface information, and posterior lens surface information, lens tilt information and lens position information; determining a desired postoperative condition of the eye; empirically calculating a postoperative condition of the eye based at least partially on the measured eye characteristics; and predictively estimating, in accordance with an output of said empirically calculating and the eye characteristics, with at least one parameter of the intraocular lens to obtain the desired postoperative condition.

A method of adjusting the refractive power in an eye of a patient who has undergone cataract surgery may comprise: measuring a plurality of post-operative eye characteristics in an eye of a patient who has previously undergone cataract surgery, the eye characteristics comprising ocular biometry information, anterior corneal surface information, posterior corneal surface information, anterior lens surface information, and posterior lens surface information, lens tilt information and lens position information; identifying a plurality of corrective procedure based at least partially on one of (1) a comparison of at least one measured pre-operative eye characteristic and the corresponding measured post-operative eye characteristic; and (2) a comparison of at least one predicted post-operative eye characteristic and the corresponding measured post-operative eye characteristic; for each of a plurality of corrective procedures: modeling the subject eye with the corrective procedure; modeling the subject eye based on the corrective procedure; performing one of a ray tracing and a power calculation based on said eye model; and selecting a corrective procedure from the plurality of IOL models corresponding to the optimized IOL based on a predetermined criteria.

In some embodiments, the system further comprises a processor configured to execute an algorithm. The algorithm comprises, for each of the IOL models: (1) modeling the subject's eye with an intraocular lens corresponding to the IOL model and the measured characteristics of the subject's eye; (2) simulating the subject's eye based on the plurality of IOL predetermined parameters and the predicted IOL position; (3) performing one of a ray tracing and a power calculation based on said model of the subject's eye; and (4) selecting an IOL from the plurality of IOL models corresponding to the optimized IOL based on a predetermined criteria.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

All patents and patent applications cited here are hereby incorporated by reference hereby reference in their entirety.

The use of the terms "a" and "an" and "the" and similar referents in the context of describing the invention (especially in the context of the following claims) are to be construed to cover both the singular and the plural, unless otherwise indicated here or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values here are merely intended to serve as a shorthand method of referring individually to each separate value falling within the range, unless otherwise indicated herein, and each separate value is incorporated into the specification as if it were individually recited herein. All methods described here can be performed in any suitable order unless otherwise indicated here or otherwise clearly contradicted by context. The use of any and all examples, or exemplary language (e.g., "such as") provided herein, is intended merely to better illuminate embodiments of the invention, and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made and remain within the concept without departing from the spirit or scope of the invention. Such variations would become clear to one of ordinary skill in the art after inspection of the specification, drawings and claims herein. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

We claim:

1. A method, comprising:
    projecting a plurality of light spots onto an eye including a cornea having a tear film disposed thereon, wherein the light spots are broadband light spots having a broad bandwidth, or are narrowband light spots whose bandwidth is tuned in time across a broad bandwidth, wherein the broad bandwidth is a frequency band whose full width at half maximum (FWHM) bandwidth is at least 40% of a center frequency of the frequency band;
    imaging the light spots from the eye onto at least one two-dimensional detector array;
    spectrally resolving each of the plurality of imaged light spots; and
    performing interferometry on the spectrally resolved imaged light spots to determine a thickness of the tear film between an anterior interface and a posterior interface of the tear film.

2. The method of claim 1, wherein the light spots are broadband light spots, and wherein spectrally resolving each of the plurality of imaged light spots comprises projecting the imaged light spots onto the at least one two-dimensional detector array via a spectrally dispersive element.

3. The method of claim 2, wherein the spectrally dispersive element is a prism.

4. The method of claim 2, wherein the spectrally dispersive element is a grating.

5. The method of claim 2, wherein the spectrally dispersive element comprises at least one interference filter.

6. The method of claim 1, wherein the light spots are narrowband light spots whose bandwidth is tuned in time across a broad bandwidth, and wherein projecting the light spots comprises:
    producing light for the light spots with at least one broadband light source;
    passing the light from at least one broadband light source through at least one frequency tunable filter to produce the narrowband light spots; and
    tuning the frequency tunable filter across the broad bandwidth over a time interval, wherein a readout of image data from the at least one two-dimensional array is synchronized to the tuning of the frequency tunable filter to spectrally resolve each of the plurality of imaged light spots.

7. The method of claim 1, wherein performing interferometry on the spectrally resolved light spots comprises determining an oscillation period of a spectrum of the spectrally resolved light spots, and wherein the thickness of the tear film is determined from the oscillation period of the spectrum.

8. An apparatus, comprising:
a plurality of light sources configured to project a plurality of broadband light spots onto an eye having a cornea and a tear film disposed thereon, the broadband light spots having a broad frequency band whose full width at half maximum (FWHM) bandwidth is at least 40% of a center frequency of the frequency band;
a two-dimensional detector array;
an optical system adapted to image the light spots from the eye onto the two-dimensional detector array, wherein the optical system includes a spectrally dispersive element, wherein the spectrally dispersive element projects the imaged light spots onto the at least one two-dimensional detector array; and
a processor configured to:
receive image data from the two-dimensional detector array,
spectrally resolve each of the plurality of imaged light spots based on the received image data from the detector array,
perform interferometry on the spectrally resolved imaged light spots to determine a thickness of the tear film between an anterior interface and a posterior interface of the tear film.

9. The apparatus of claim 8, wherein the spectrally dispersive element is a prism.

10. The apparatus of claim 8, wherein the spectrally dispersive element is a grating.

11. The apparatus of claim 8, wherein the spectrally dispersive element comprises at least one interference filter.

12. The apparatus of claim 8, further comprising a second two-dimensional detector array, wherein the optical system is adapted to image the light spots from the cornea onto the second two-dimensional detector array, and wherein the processor is configured to determine a corneal topography from an output of the second two-dimensional detector array.

13. The apparatus of claim 8, wherein the plurality of light sources comprises:
a group of first light sources arranged around a central axis of the optical system, the group being separated from the axis by a radial distance defining an aperture in the group; and
a Helmholz light source for projecting some of the light spots onto the cornea through the aperture, wherein the optical system includes an optical element having a focal length, f, and wherein the Helmholz light source is disposed to be in an optical path approximately one focal length, f, away from the optical element.

14. The apparatus of claim 13, further comprising a structure having a principal surface with an opening therein around the central axis, wherein the group of first light sources is provided on the principal surface.

15. The apparatus of claim 14, wherein the first light sources are arranged on the structure such that when the cornea has a predetermined shape, the images of the first light sources are uniformly spaced on a grid on the two-dimensional detector array.

16. The apparatus of claim 8, wherein the processor is configured to perform interferometry on the spectrally resolved light spots by determining an oscillation period of a spectrum of the spectrally resolved light spots, and wherein the thickness of the tear film is determined from the oscillation period of the spectrum.

17. An apparatus, comprising:
at least one broadband light source configured to produce broadband light;
a frequency tunable filter configured to receive the broadband light, wherein the frequency tunable filter is configured to output narrowband light, and wherein the frequency tunable filter is further configured to be tuned across a broad bandwidth over a time interval, wherein the broad bandwidth is a frequency band whose full width at half maximum (FWHM) bandwidth is at least 40% of a center frequency of the frequency band;
a light projection arrangement configured to receive the narrowband light from the frequency tunable filter and to project a plurality of narrowband light spots onto an eye having a cornea and a tear film disposed thereon;
a two-dimensional detector array;
an optical system adapted to image the light spots from the cornea onto the two-dimensional detector array; and
a processor configured to:
receive image data from the two-dimensional detector array, synchronized with the tuning of the frequency tunable filter across the broad bandwidth to spectrally resolve each of the plurality of imaged light spots,
perform interferometry on the spectrally resolved imaged light spots to determine a thickness of the tear film between an anterior interface and a posterior interface.

18. The apparatus of claim 17, wherein the light projection arrangement comprises:
a group of first light emitters arranged around a central axis of the optical system, the group being separated from the axis by a radial distance defining an aperture in the group; and a
Helmholz light source for projecting some of the light spots onto the cornea through the aperture, wherein the optical system includes an optical element having a focal length, f, and wherein the Helmholz light source is disposed to be in an optical path approximately one focal length, f, away from the optical element.

19. The apparatus of claim 18, further comprising a structure having a principal surface with an opening therein around the central axis, wherein the group of first light emitters is provided on the principal surface.

20. The apparatus of claim 19, wherein the first light emitters are arranged on the structure such that when the cornea has a predetermined shape, the images of the first light sources are uniformly spaced on a grid on the two-dimensional detector array.

* * * * *